US012600707B2

(12) United States Patent
Abdur-Rashid et al.

(10) Patent No.: US 12,600,707 B2
(45) Date of Patent: Apr. 14, 2026

(54) CANNABINOID DERIVATIVES, PRECURSORS AND USES

(71) Applicant: KARE CHEMICAL TECHNOLOGIES INC., Mississauga (CA)

(72) Inventors: Kamaluddin Abdur-Rashid, Mississauga (CA); Wenli Jia, Toronto (CA); Kareem Abdur-Rashid, Mississauga (CA)

(73) Assignee: KARE CHEMICAL TECHNOLOGIES INC., Mississauga (CA)

( * ) Notice: Subject to any disclaimer, the term of this patent is extended or adjusted under 35 U.S.C. 154(b) by 801 days.

(21) Appl. No.: 17/753,616

(22) PCT Filed: Sep. 3, 2020

(86) PCT No.: PCT/CA2020/051198
§ 371 (c)(1),
(2) Date: Mar. 9, 2022

(87) PCT Pub. No.: WO2021/046636
PCT Pub. Date: Mar. 18, 2021

(65) Prior Publication Data

US 2022/0380333 A1 Dec. 1, 2022

Related U.S. Application Data

(60) Provisional application No. 62/897,818, filed on Sep. 9, 2019.

(51) Int. Cl.
*C07D 311/80* (2006.01)
*C07C 29/153* (2006.01)
*C07C 29/64* (2006.01)

(52) U.S. Cl.
CPC .......... *C07D 311/80* (2013.01); *C07C 29/153* (2013.01); *C07C 29/64* (2013.01); *C07B 2200/05* (2013.01)

(58) Field of Classification Search
CPC .................................................... C07D 311/80
See application file for complete search history.

(56) References Cited

U.S. PATENT DOCUMENTS

| | | | |
|---|---|---|---|
| 5,036,014 | A | 7/1991 | Elsohly et al. |
| 2010/0152283 | A1 | 6/2010 | Gant |
| 2012/0172339 | A1 | 7/2012 | Makriyannis et al. |
| 2023/0059087 | A1 | 2/2023 | Zhou et al. |

FOREIGN PATENT DOCUMENTS

| | | | |
|---|---|---|---|
| CN | 110143847 A | | 8/2019 |
| EP | 2687854 A1 | | 1/2014 |
| JP | 2009510078 A | | 3/2009 |
| JP | 2009536623 A | | 10/2009 |
| WO | WO-2011006099 A1 | | 1/2011 |
| WO | WO-2017011210 A1 | | 1/2017 |
| WO | WO-2020117288 A1 | | 6/2020 |
| WO | WO-2021046636 A1 | | 3/2021 |
| WO | WO-2021139741 A1 | | 7/2021 |
| WO | WO-2021150885 A1 | | 7/2021 |

OTHER PUBLICATIONS

Hanzlik, R. P. "Selective epoxidation of terminal double bonds: 10, 11-epoxyfarnesyl acetate." Organic Syntheses 56 (1977): 112. (Year: 1977).*

Marzabadi, Cecilia H., Christopher D. Spilling, and Lisa M. Tyler. "The chemistry of glucal halohydrins: The effect of the halide on epoxide formation." Tetrahedron 50.23 (1994): 6783-6796. (Year: 1994).*

Ashenhurst, J. (Jul. 1, 2017). Epoxides—The Outlier of the Ether Family. Mastering Organic Chemistry. Internet Archive Wayback Machine. Archived from https://www.masterorganicchemistry.com/2015/01/26/epoxides-the-outlier-of-the-ether-family/ on Jul. 1, 2017. Retrieved Sep. 4, 2025. (Year: 2017).*

"CAS Registry No. 81586-36-9", (Nov. 16, 1984), 1 pg.

"International Application No. PCT/CA2020/051198, International Search Report and Written Opinion mailed Dec. 15, 2020", (Dec. 15, 2020), 14 pgs.

Banijamali, Ali R., et al., "Synthesis of Deuterium Labeled Cannabinoids", Journal of Labelled Compounds and Radiopharmaceuticals, 1988, 25(1), (1988), 73-82.

Fisher, Kenneth, et al., "Experiments on the Synthesis of the Terpenes. Part I (continued). Resolution of dl-1-Methyl-A1-cyclohexene-4-carboxylic Acid and Synthesis of the Optically Active Modifications of Terpineol", J. Chem. Soc. 1908, 93, (1908), 1871-1876.

Ho, Tse-Lok, et al., "Total Synthesis of (+)-b-Himachalene", Helvetica Chimica Acta, vol. 89 (2006), (2006), 231-239.

Mechoulam, Raphael, et al., "Syntheses of Alpha-1 Tetrahydrocannabinol and related Cannabinoids", J. Am. Chem. Soc., 1972, 94(17), (Aug. 23, 1972), 6159-6165.

"Chinese Application No. 202080077549.4, Office Action dated Jan. 11, 2024", w/ English Translation, (Jan. 11, 2024), 24 pgs.

"European Application No. 20863462.6, Office Action dated Sep. 22, 2023", (Sep. 22, 2023), 21 pgs.

"Indian Application No. 202247021081, Office Action dated Oct. 25, 2024", (Oct. 25, 2024), 9 pgs.

"Israeli Application No. 291253, Notice of Deficiencies dated Feb. 27, 2023", (Feb. 27, 2023), 6 pgs.

"Japanese Application No. 2022-515962, Office Action dated Jul. 31, 2024", w/ English Translation, (Jul. 31, 2024), 13 pgs.

Banijamali, Ali R., et al., "Addition and elimination of HCl to tetrahydrocannabinol isomers. A method for the preparation of stereospecifically 2H-labeled cannabinoids", Journal of Labelled Compounds and Radiopharmaceuticals 41.2, (1998), 121-130.

(Continued)

*Primary Examiner* — Andrew D Kosar
*Assistant Examiner* — Connor K English
(74) *Attorney, Agent, or Firm* — Schwegman Lundberg & Woessner, P.A.

(57) ABSTRACT

The present disclosure relates to new cannabinoid derivatives and precursors and processes for their preparation. The disclosure also relates to pharmaceutical and analytical uses of the new cannabinoid derivatives.

10 Claims, 1 Drawing Sheet

(56) References Cited

OTHER PUBLICATIONS

Hauenstein, Oliver, et al., "Bio-based polycarbonate from limonene oxide and CO 2 with high molecular weight, excellent thermal resistance, hardness and transparency", Green Chemistry 18.3, (2016), 760-770.
Pitt, C. G., "The synthesis of deuterium, carbon-14, and carrier-free tritium labeled cannabinoids", Journal of Labelled Compounds 11.4, (1975), 551-575.
Wilkinson, Shane M., et al., "Improved accessibility to the desoxy analogues of ?9-tetrahydrocannabinol and cannabidiol", Tetrahedron Letters 54.1, (2013), 52-54.

* cited by examiner

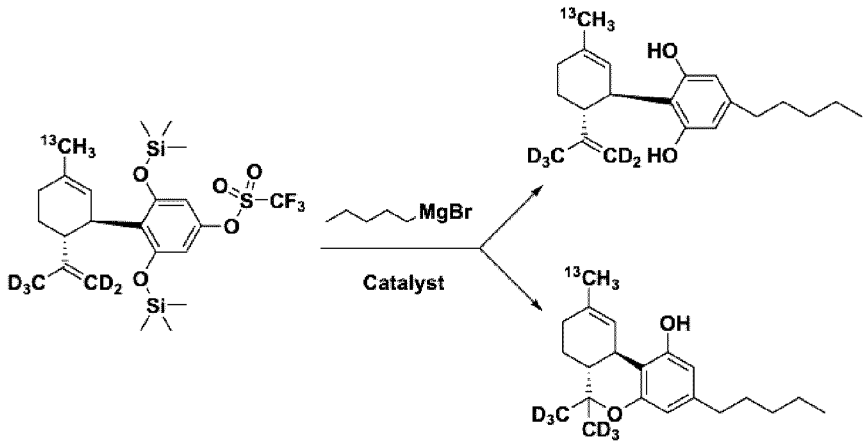
MgBr
Catalyst

CANNABINOID DERIVATIVES, PRECURSORS AND USES

CROSS-REFERENCE TO RELATED APPLICATIONS

This application is a U.S. national stage filing under 35 U.S.C. § 371 from International Application No. PCT/CA2020/051198, filed on Sep. 3, 2020, and published as WO2021/046636 on Mar. 18, 2021, which claims the benefit of priority to U.S. Provisional Application No. 62/897,818, filed Sep. 9, 2019, the benefit of priority of each of which is claimed herein, and which applications and publication are hereby incorporated herein by reference in its entirety.

FIELD OF THE DISCLOSURE

The present disclosure relates to new cannabinoid derivatives and precursors and processes for their preparation. The disclosure also relates to pharmaceutical and analytical uses of the new cannabinoid derivatives.

BACKGROUND OF THE DISCLOSURE

Cannabinoids are diverse chemical compounds that acts on cannabinoid receptors that alter neurotransmitter release in the brain. Cannabinoids include the endocannabinoids produced naturally in the body by animals; phytocannabinoids found in *cannabis* and perrotettinenes found in liverworts. The most notable cannabinoids are tetrahydrocannabinol (THC), the primary psychoactive compound in *cannabis*, and Cannabidiol (CBD). There are more than 100 different cannabinoids isolated from *cannabis*, exhibiting varying effects.

Cannabidiol (CBD) is the non-psychoactive and primary medicinal component of the *cannabis* plant. As such, CBD has significant medicinal benefits. It has been shown to counteract the psychoactive effect of tetrahydrocannabinol (THC); the other main component of *cannabis*. Hence, over the years a variety of CBD-rich strains of *cannabis* has been developed and used medicinally for treating inflammation, AIDS, ALS, Alzheimer's disease, anorexia, anxiety, arthritis, asthma, cancer, depression, diabetes, epilepsy, glaucoma, migraine, nausea, neuropathic pain, Parkinson's disease, just to name a few. In addition, there are numerous clinical trials being conducted worldwide for pharmaceutical applications of CBD, THC, Cannabidivarin (CBDV), Tetrahydrocannabidivarin (THV) and other cannabinoids for these and numerous other illnesses.

p-Menthadienol ((1S,4R)-1-methyl-4-(prop-1-en-2-yl)cyclohex-2-enol) derived from commercial limonene oxide is a precursor for the preparation of synthetic cannabinoids. One of the drawbacks in the manufacture of p-menthadienol is that the yield is relatively low, because commercial limonene oxide is a mixture of cis-limonene oxide and trans-limonene oxide in about equal amounts. The trans-limonene oxide is required for the desired p-menthadienol product. Hence, the overall yield of preparing p-menthadienol from commercial limonene oxide can vary from 10% to a high of 35% (T.-L. Ho and R.-J. Chein, Helvetica Chimica Acta 2006, 89, 231-239).

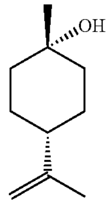

p-Menthadienol

SUMMARY OF THE DISCLOSURE

The present disclosure describes a new method of preparing p-menthadienol from limonene. Limonene is much cheaper and more widely available than limonene oxide. The disclosure also describes methods for preparing p-menthadienol containing deuterium, carbon-13 and carbon-14 isotopes. The precursors containing the deuterium and carbon isotopes are used to prepare new cannabinoids labelled with the isotopes. The processes focus on the use of commercially available chemicals and a new method to prepare stable precursors that can be transformed into the desired isotope labelled cannabinoid products on demand.

In various aspects, the disclosure relates to a new method for the preparation of p-menthadienol and p-menthadienol derivatives containing deuterium, carbon-13 and carbon-14, and the use of such derivatives as precursor compounds for the preparation of deuterated, carbon-13 and carbon-14 cannabinoid products using catalysts and catalytic processes. The isotope containing compounds can be prepared and purified prior to transformation to the desired individual cannabinoid products. The isotope containing precursors are air-stable and shelf-stable compounds that can be stored, transported, and converted into the desired isotope containing cannabinoid products on demand.

In an embodiment of the disclosure, the deuterium and carbon-13 cannabinoids have isotopic enrichments of no less than 1% at the specified position. In another embodiment, the enrichment is no less than 5% at the specified position. In another embodiment, the enrichment is no less than 10% at the specified position. In another embodiment, the enrichment is no less than 20% at the specified position. In another embodiment, the enrichment is no less than 50% at the specified position. In another embodiment, the enrichment is no less than 70% at the specified position. In another embodiment, the enrichment is no less than 80% at the specified position. In another embodiment, the enrichment is no less than 90% at the specified position. In another embodiment, the enrichment is no less than 98% at the specified position.

In an embodiment of the disclosure, the carbon-14 cannabinoids have isotopic enrichments of no less than 1 part per billion at the specified position. In another embodiment, the enrichment is no less than 1 part per million at the specified position. In another embodiment, the enrichment is no less than 0.1% at the specified position. In another embodiment, the enrichment is no less than 10% at the specified position.

Other features and advantages of the present application will become apparent from the following detailed description. However, it should be understood that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The disclosure will be described in greater detail with reference to the following drawings in which, which are meant to be illustrative by certain embodiments of the disclosure and are not meant to limit the scope of the disclosure:

FIG. 1 shows the synthesis of compounds of compounds of the disclosure.

DETAILED DESCRIPTION OF THE DISCLOSURE

(I) Definitions

The term "alkyl" as used herein means straight and/or branched chain, saturated alkyl radicals containing one or more carbon atoms and includes (depending on the identity) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

The term "alkenyl" as used herein means straight and/or branched chain, unsaturated alkyl radicals containing two or more carbon atoms and one to three double bonds, and includes (depending on the identity) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

The term "alkynyl" as used herein means straight and/or branched chain, unsaturated alkyl radicals containing two or more carbon atoms and one to three triple bonds, and includes (depending on the identity) acetylynyl, propynyl, but-1-ynyl, but-2-ynyl, but-3-ynyl, 3-methylbut-1-enyl, 3-methylpent-1-ynyl, 4-methylpent-1-ynyl, 4-methylpent-2-ynyl, penta-1,3-di-ynyl, hexyn-1-yl and the like.

The term "alkoxy" as used herein means straight and/or branched chain alkoxy group containing one or more carbon atoms and includes (depending on the identity) methoxy, ethoxy, propyloxy, isopropyloxy, t-butoxy, heptoxy, and the like.

The term "cycloalkyl" as used herein means a monocyclic, bicyclic or tricyclic saturated carbocylic group containing three or more carbon atoms and includes (depending on the identity) cyclopropyl, cyclobutyl, cyclopentyl, cyclodecyl and the like. The term "aryl" as used herein means a monocyclic, bicyclic or tricyclic aromatic ring system containing at least one aromatic ring and 6 or more carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl" as used herein means a monocyclic, bicyclic or tricyclic ring system containing one or two aromatic rings and 5 or more atoms of which, unless otherwise specified, one, two, three, four or five are heteromoieties independently selected from N, NH, N(alkyl), O and S and includes thienyl, furyl, pyrrolyl, pyrididyl, indolyl, quinolyl, isoquinolyl, tetrahydroquinolyl, benzofuryl, benzothienyl and the like.

The term "halo" as used herein means halogen and includes chloro, fluoro, bromo or iodo.

The term "fluoro-substituted" as used herein means that at least one, including all, of the hydrogens on the referenced group is replaced with fluorine.

The suffix "ene" added on to any of the above groups means that the group is divalent, i.e. inserted between two other groups.

The term "ring system" as used herein refers to a carbon-containing ring system, that includes monocycles, fused bicyclic and polycyclic rings, bridged rings and metallocenes. Where specified, the carbons in the rings may be substituted or replaced with heteroatoms.

The term "isotope enrichment" refers to the percentage of incorporation of deuterium, carbon-13 and carbon-14 at a given position in a molecule in the place of hydrogen and carbon-12. For example, deuterium enrichment of 1% at a given position means that 1% of molecules in a given sample contains deuterium at the specified position. Because the naturally occurring distribution of deuterium is about 0.0156%, deuterium enrichment at any position using non-enriched precursors is about 0.0156%. In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. For instance, "including" also encompasses "including but not limited to". Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Compounds of the Disclosure

Accordingly, in some embodiments, the present disclosure relates to compounds of Formula (I):

(I)

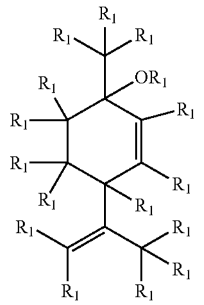

wherein, the $R_1$ groups are independently or simultaneously selected from the group consisting of hydrogen and deuterium; and at least one $R_1$ is deuterium.

In another embodiment of the disclosure, at least one carbon atom of Formula (I) is a carbon-13 or carbon-14 atom.

In some embodiments, the present disclosure relates to a compound of Formula (II):

(II)

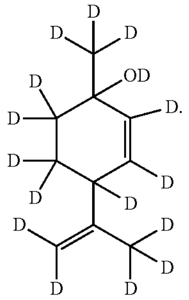

In some embodiments, the present disclosure relates to a compound of Formula (III):

(III)

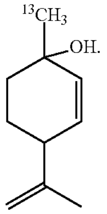

In some embodiments, the present disclosure relates to a compound of Formula (IV):

(IV)

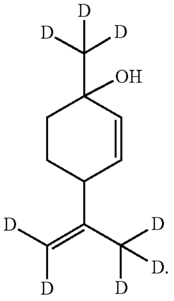

In some embodiments, the present disclosure relates to compounds of Formula (V), Formula (VI) and Formula (VII):

(V)

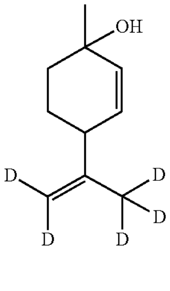

-continued (VI)

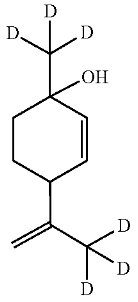

(VII)

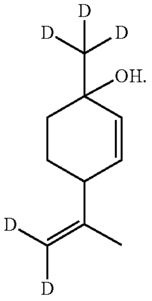

In some embodiments, the present disclosure relates to compounds of Formula (VIII), Formula (IX) and Formula (X):

(VIII)

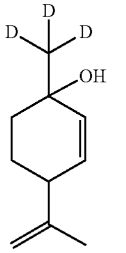

(IX)

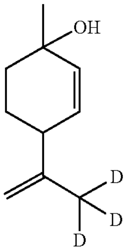

(X)

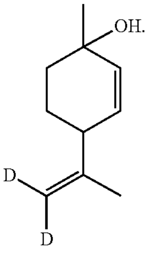

In some embodiments of the disclosure, at least one carbon atom of Formula (II) to Formula (X) is a carbon-13 or carbon-14 atom.

In an embodiment of the disclosure, Formula (I) to Formula (X) can include a single enantiomer, a mixture of enantiomers, an individual diastereomer, or a mixture of diastereomers.

In another embodiment, the compound of Formula (I) is

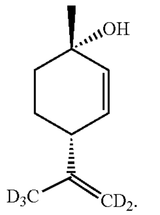

In another embodiment, the present disclosure relates to compounds of Formula (XI):

(XI)

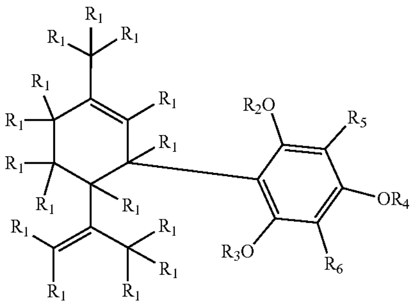

wherein, the $R_1$ groups are independently or simultaneously selected from the group consisting of hydrogen and deuterium; and at least one $R_1$ is deuterium;

$R_2$ to $R_4$ represent hydrogen, deuterium, a linear or branched alkyl group of any length, possibly substituted, an alkenyl group of any length, possibly substituted, an alkynyl group, possibly substituted, a cycloalkyl group, possibly substituted, an aryl group, possibly substituted, a heteroaryl group, possibly substituted, or an acyl group, possibly substituted, wherein one or more of the carbon atoms in the alkyl, alkenyl, alkynyl, cycloalkyl, aryl, heteroaryl or acyl groups of $R_2$ to $R_4$ is optionally replaced with a heteroatom selected from the group consisting of O, S, N, P and Si, which, where possible, is optionally substituted with one or more groups; and $R_5$ and $R_6$ represent hydrogen, deuterium, halide, a linear or branched alkyl group of any length, possibly substituted, an alkenyl group of any length, possibly substituted, an alkynyl group, possibly substituted, a cycloalkyl group, possibly substituted, an aryl group, possibly substituted, an heteroaryl group, possibly substituted, an acyl group, possibly substituted, or a carboxylate group, possibly substituted, wherein one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups.

In another embodiment of the disclosure, at least one of the carbon atoms connected to at least one $R_1$ of Formula (XI) is carbon-13 or carbon-14; and $R_1$ is selected from hydrogen or deuterium.

In a general way, the compounds of Formula (XI) can be prepared and isolated prior to use.

In further embodiments, the present disclosure also relates to compounds of Formula (XII):

(XII)

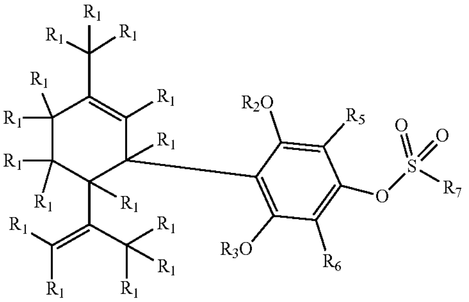

wherein, the $R_1$ groups are independently or simultaneously selected from the group consisting of hydrogen and deuterium; and at least one $R_1$ is deuterium;

$R_2$ and $R_3$ represent hydrogen, deuterium, a linear or branched alkyl group of any length, possibly substituted, an alkenyl group of any length, possibly substituted, an alkynyl group, possibly substituted, a cycloalkyl group, possibly substituted, an aryl group, possibly substituted, a heteroaryl group, possibly substituted, or an acyl group, possibly substituted, wherein one or more of the carbon atoms in the alkyl, alkenyl, alkynyl, cycloalkyl, aryl, heteroaryl or acyl groups of $R_2$ to $R_3$ is optionally replaced with a heteroatom selected from the group consisting of O, S, N, P and Si, which, where possible, is optionally substituted with one or more groups; and $R_5$ and $R_6$ represent hydrogen, deuterium, halide, a linear or branched alkyl group of any length, possibly substituted, an alkenyl group of any length, possibly substituted, an alkynyl group, possibly substituted, a cycloalkyl group, possibly substituted, an aryl group, possibly substituted, an heteroaryl group, possibly substituted, an acyl group, possibly substituted, or a carboxylate group, possibly substituted, wherein one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups;

$R_7$ represents a hydrogen atom, a linear or branched alkyl group of any length, possibly substituted, an alkenyl group of any length, possibly substituted, an alkynyl group, possibly substituted, a cycloalkyl group, possibly substituted, an aryl group, possibly substituted, a heteroaryl group, possibly substituted, an $OR^c$ group or an $NR^c_2$ group, possibly substituted, with possible and non-limiting substituents of $R_7$ being halogen atoms, $OR^c$, or $NR^c_2$ groups, in which $R^c$ is a hydrogen atom or a cyclic, linear or branched alkyl, aryl or alkenyl group.

In another embodiment of the disclosure, at least one of the carbon atoms connected to at least one $R_1$ of Formula (XII) is carbon-13 or carbon-14; and $R_1$ is selected from hydrogen or deuterium.

In a general way, the compounds of Formula (XII) can be prepared and isolated prior to use.

In another embodiment, the present disclosure relates to compounds of Formula (XIII):

(XIII)

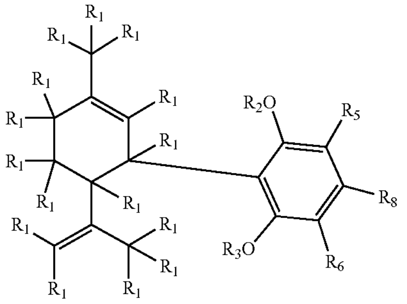

wherein, the $R_1$ groups are independently or simultaneously selected from the group consisting of hydrogen and deuterium; and at least one $R_1$ is deuterium;

$R_2$ and $R_3$ represent hydrogen, deuterium, a linear or branched alkyl group of any length, possibly substituted, an alkenyl group of any length, possibly substituted, an alkynyl group, possibly substituted, a cycloalkyl group, possibly substituted, an aryl group, possibly substituted, a heteroaryl group, possibly substituted, or an acyl group, possibly substituted, wherein one or more of the carbon atoms in the alkyl, alkenyl, alkynyl, cycloalkyl, aryl, heteroaryl or acyl groups of $R_2$ to $R_3$ is optionally replaced with a heteroatom selected from the group consisting of O, S, N, P and Si, which, where possible, is optionally substituted with one or more groups; and $R_5$ and $R_6$ represent hydrogen, deuterium, halide, a linear or branched alkyl group of any length, possibly substituted, an alkenyl group of any length, possibly substituted, an alkynyl group, possibly substituted, a cycloalkyl group, possibly substituted, an aryl group, possibly substituted, an heteroaryl group, possibly substituted, an acyl group, possibly substituted, or a carboxylate group, possibly substituted, wherein one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups; and $R_8$ represents a hydrogen atom, a linear or branched alkyl group of any length, possibly substituted, an alkenyl group of any length, possibly substituted, an alkynyl group, possibly substituted, a cycloalkyl group, possibly substituted, or an aryl group, possibly substituted.

In another embodiment of the disclosure, at least one of the carbon atoms connected to at least one $R_1$ of Formula (XIII) is carbon-13 or carbon-14; and $R_1$ is selected from hydrogen or deuterium.

In one embodiment, the compound of Formula (XIII) is

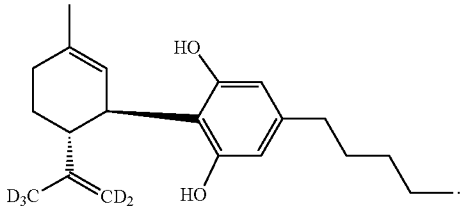

In a general way, the compounds of Formula (XIII) can be prepared and isolated prior to use.

In another embodiment, the present disclosure relates to compounds of Formula (XIV):

(XIV)

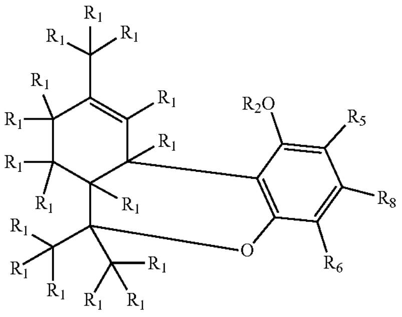

wherein, the $R_1$ groups are independently selected from the group consisting of hydrogen and deuterium; and at least one $R_1$ is deuterium;

$R_2$ represents hydrogen, deuterium, a linear or branched alkyl group of any length, possibly substituted, an alkenyl group of any length, possibly substituted, an alkynyl group, possibly substituted, a cycloalkyl group, possibly substituted, an aryl group, possibly substituted, a heteroaryl group, possibly substituted, an acyl group, possibly substituted, wherein one or more of the carbon atoms in the alkyl, alkenyl, alkynyl, cycloalkyl, aryl, heteroaryl or acyl groups of $R_2$ is optionally replaced with a heteroatom selected from the group consisting of O, S, N, P and Si, which, where possible, is optionally substituted with one or more groups;

$R_5$ and $R_6$ represent hydrogen, deuterium, halide, a linear or branched alkyl group of any length, possibly substituted, an alkenyl group of any length, possibly substituted, an alkynyl group, possibly substituted, a cycloalkyl group, possibly substituted, an aryl group, possibly substituted, an heteroaryl group, possibly substituted, an acyl group, possibly substituted, or a carboxylate group, possibly substituted, wherein one or more of the carbon atoms in the alkyl, alkenyl, alkynyl, cycloalkyl, aryl, heteroaryl, acyl or carboxylate groups of $R_5$ and/or $R_6$ is optionally replaced with a heteroatom selected from the group consisting of O, S, N, P and Si, which, where possible, is optionally substituted with one or more groups; and $R_8$ represents a hydrogen atom, a linear or branched alkyl group of any length, possibly substituted, an alkenyl group of any length, possibly substituted, an alkynyl group, possibly substituted, a cycloalkyl group, possibly substituted, or an aryl group, possibly substituted.

In another embodiment of the disclosure, at least one of the carbon atoms connected to at least one $R_1$ of Formula (XIV) is carbon-13 or carbon-14; and $R_1$ is selected from hydrogen or deuterium.

In one embodiment, the compound of Formula (XIV) is

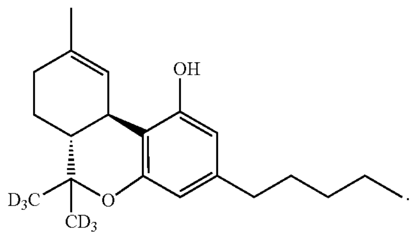 [SMILES: [2H]C([2H])([2H])C1(C([2H])([2H])[2H])Oc2cc(CCCCC)cc(O)c2[C@@H]2C=C(C)CC[C@H]21]

In a general way, the compounds of Formula (XIV) can be prepared and isolated prior to use.

In one embodiment, the alkyl groups of any length in any of the Formulas of the disclosure is optionally substituted $C_1$-$C_{20}$-alkyl. In another embodiment, the alkyl group is optionally substituted $C_1$-$C_{10}$-alkyl. In another embodiment, the alkyl group is optionally substituted $C_1$-$C_6$-alkyl. In another embodiment, the alkyl group is methyl, ethyl, propyl, butyl or pentyl. In another embodiment, the optional substituents are hydroxyl, halo or $C_1$-$C_6$-alkyl.

In one embodiment, the alkenyl groups of any length in any of the Formulas of the disclosure is optionally substituted $C_2$-$C_{20}$-alkenyl. In another embodiment, the alkenyl group is optionally substituted $C_2$-$C_{10}$-alkenyl. In another embodiment, the alkenyl group is optionally substituted $C_2$-$C_6$-alkenyl. In another embodiment, the alkenyl group is ethenyl, propenyl, butenyl or pentenyl. In another embodiment, the optional substituents are hydroxyl, halo or $C_1$-$C_6$-alkyl.

In one embodiment, the alkynyl groups of any length in any of the Formulas of the disclosure is optionally substituted $C_2$-$C_{20}$-alkynyl. In another embodiment, the alkynyl group is optionally substituted $C_2$-$C_{10}$-alkynyl. In another embodiment, the alkynyl group is optionally substituted $C_2$-$C_6$-alkynyl. In another embodiment, the alkynyl group is ethynyl, propynyl, butynyl or pentynyl. In another embodiment, the optional substituents are hydroxyl, halo or $C_1$-$C_6$-alkyl.

In one embodiment, the cycloalkyl groups in any of the Formulas of the disclosure is optionally substituted $C_3$-$C_{20}$-cycloalkyl. In another embodiment, the cycloalkyl group is optionally substituted $C_3$-$C_{10}$-cycloalkyl. In another embodiment, the cycloalkyl group is optionally substituted $C_3$-$C_6$-cycloalkyl. In another embodiment, the cycloalkyl group is cyclopropyl, cyclobutyl or cyclopentyl. In another embodiment, the optional substituents are hydroxyl, halo or $C_1$-$C_6$-alkyl.

In one embodiment, the aryl groups in any of the Formulas of the disclosure is optionally substituted $C_6$-$C_{14}$-aryl. In another embodiment, the aryl group is optionally substituted $C_6$-$C_{10}$-aryl, or phenyl. In another embodiment, the aryl group is phenyl, naphthyl, tetrahydronaphthyl, phenanthrenyl, biphenylenyl, indanyl, or indenyl and the like. In another embodiment, the optional substituents are hydroxyl, halo or $C_1$-$C_6$-alkyl. In one embodiment, the heteroaryl groups in any of the Formulas of the disclosure is optionally substituted $C_5$-$C_{14}$-heteroaryl. In another embodiment, the heteroaryl group is optionally substituted $C_6$-$C_{10}$-heteroaryl, or $C_1$-$C_6$-heteroaryl. In another embodiment, the heteroaryl group is benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, quinolinyl, quinazolinyl, triazolyl, thiazolyl, thiophenyl, tetrahydroindolyl, tetrazolyl, thiadiazolyl, thienyl, triazolyl and the like. In another embodiment, the optional substituents are hydroxyl, halo or $C_1$-$C_6$-alkyl.

In some other aspects of the disclosure, the present disclosure provides a method for the synthesis of one or more of the cannabinoid products below:

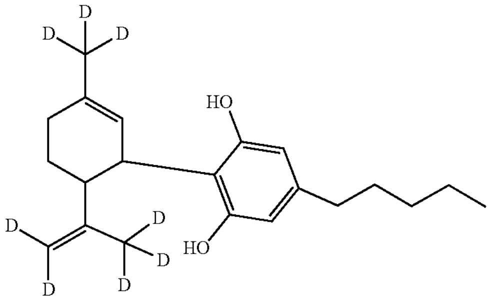

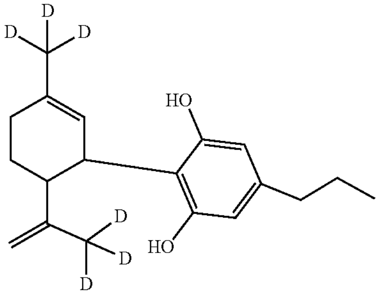

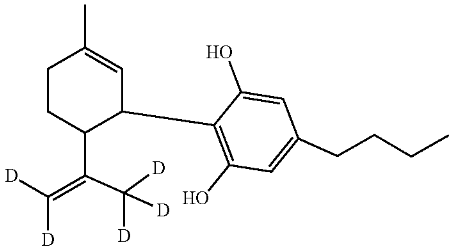

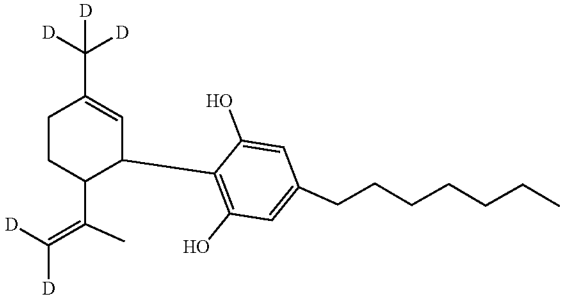

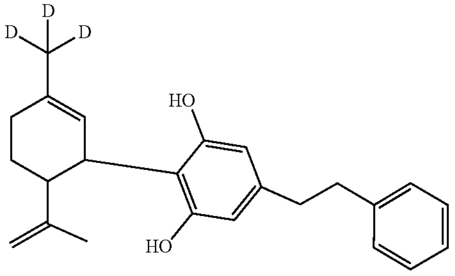

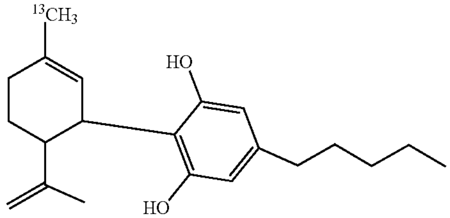

In some other aspects of the disclosure, the present disclosure provides a method for the synthesis of one or more of the cannabinoid products below:

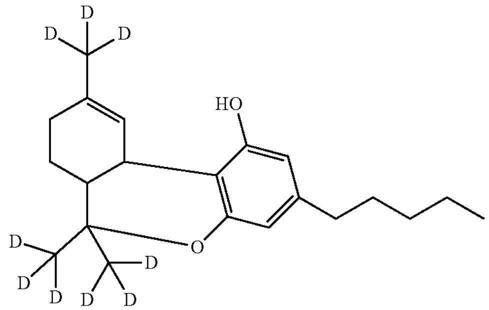

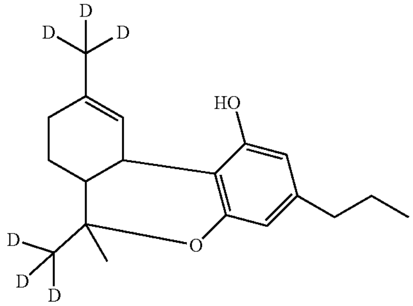

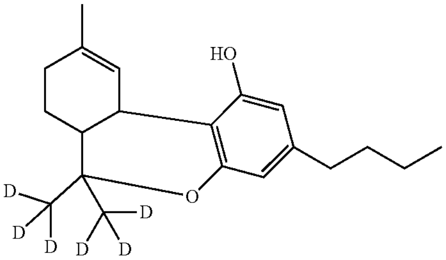

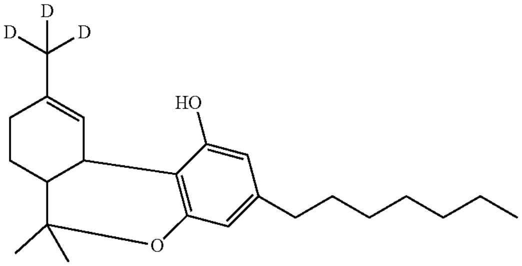

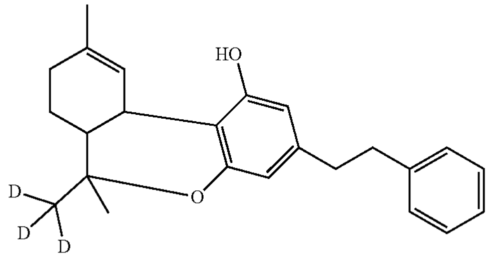

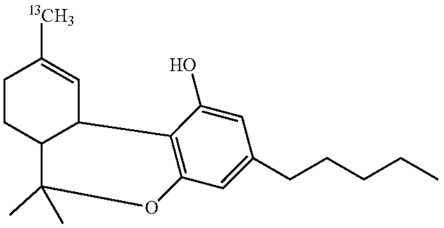

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

(III) Processes of the Disclosure

In further embodiments, the present disclosure also relates to processes for the production of compounds of the disclosure.

In one embodiment, the present disclosure relates to a process for the preparation of a compound of Formula (I) comprising:

(a) reacting a limonene precursor with a N-halosuccinimide to prepare a halohydrin; wherein halo represents fluoro, chloro, bromo, iodo;

(b) reacting the halohydrin with a base (such as an alkali metal base) to prepare a trans-limonene oxide;

(c) reacting the trans-limonene oxide with $(R_9)_2NH$ to prepare an aminoalcohol; wherein $R_9$ represents hydrogen, optionally substituted $C_1$-$C_{20}$-alkyl, optionally substituted $C_2$-$C_{20}$-alkenyl, optionally substituted $C_2$-$C_{20}$-alkynyl, optionally substituted $C_3$-$C_{20}$-cycloalkyl, optionally substituted $C_6$-$C_{14}$-aryl;

(d) converting the aminoalcohol to a compound of Formula (I), by reacting the aminoalcohol with hydrogen peroxide and heat.

In one embodiment there is disclosed a procedure for the preparation of p-menthadienol involving:

(a) reacting limonene with a N-bromosuccinimide to prepare a bromohydrin;

(b) reacting the bromohydrin with concentrated alkali solution (sodium hydroxide) to prepare trans-limonene oxide; and (c) converting the trans-limonene oxide to p-menthadienol.

In one embodiment, the process allows isolation of p-menthadienol in yields of 60% to 80% based on limonene.

In one embodiment, there is a process for the preparation of p-menthadienol or a derivative thereof, comprising:

(a) reacting limonene (or a derivative) with N-bromosuccinimide to prepare a bromohydrin;

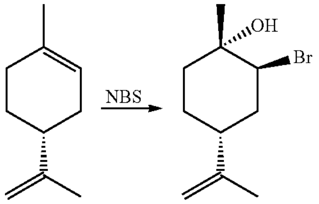

(b) reacting the bromohydrin with an alkali solution to prepare trans-limonene oxide;

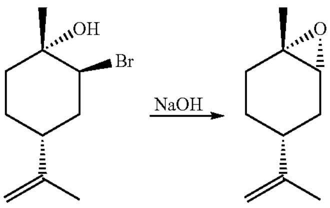

(c) reacting the trans-limonene oxide with di-methylamine to prepare an aminoalcohol;

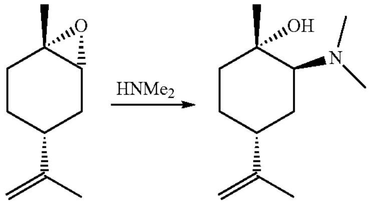

(e) converting the aminoalcohol to p-menthadienol, by reacting the aminoalcohol with hydrogen peroxide and heat.

In one embodiment, the disclosure includes the preparation of a compound of Formula (I), wherein the limonene is a deuterated-, carbon-13- and/or carbon-14 analogue of limonene.

bly substituted, an alkynyl group, possibly substituted, a cycloalkyl group, possibly substituted, or an aryl group, possibly substituted.

The disclosure also relates to a process for the catalytic and non-catalytic production of the compounds of the disclosure. Such processes include carbon-carbon bond forming reactions including, but not limited to catalytic and non-catalytic Ullman, Suzuki-Miyaura, Negishi, Kumada, Sonogashira and Stille reactions.

In some embodiments of the disclosure, the reactions require a boron containing compound such as $R_8$-$B(OH)_2$, $R_8$-$B(OR)_2$ or $R_8$—$BF_3K$; or a Grignard compound such as $R_8$—MgX; or an organozinc compound, such as $R_8$—ZnX, in the presence or absence of a catalyst, wherein $R_8$ is as defined above, and X is a halide.

In another embodiment of the disclosure, compounds of the Formula (XIII) and (XIV) are formed from compounds of the Formula (XII) in the following manner shown in Scheme 1, as shown in FIG. 1:

Scheme 1

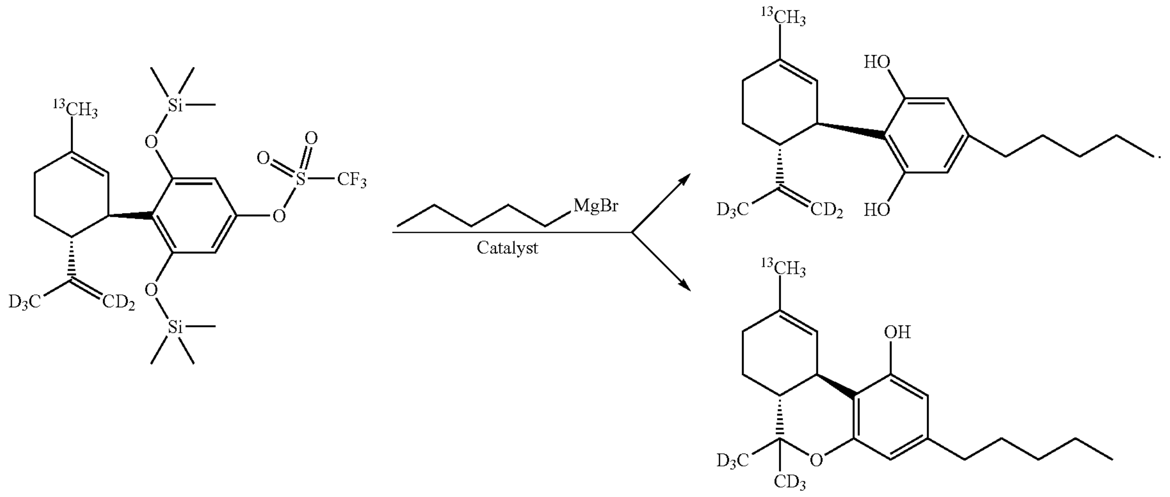

Another embodiment of the disclosure involves contacting a p-menthadienol compound of Formula (I) with a resorcinol compound in the presence of an acid or a Lewis acid catalyst to give a compound of Formula (XI). In one embodiment, the resorcinol compound is 1,3,5-tihydroxybenzene (phloroglucinol).

Another embodiment of the disclosure involves contacting a compound of Formula (XI) with a suitable sulfonating agent in the presence of a base to form a compound of Formula (XII). In one embodiment, the sulfonating agent is N-phenyl-bis(trifluoromethanesulfonimide).

The reaction of a compound of Formula (XII) with a nucleophilic $R_8$—M compound in the presence or absence of a catalyst gives a cannabinoid compound of Formula (XIII), wherein $R_8$—M is a boron containing compound such as $R_8$—$B(OH)_2$, $R_8$-$B(OR)_2$ or $R_8$—$BF_3K$; or a Grignard compound such as $R_8$—MgX; or an organozinc compound such as $R_8$—ZnX; where is X a halide (such as fluoro, chloro, bromo or iodo); and $R_8$ represents a hydrogen atom, a linear or branched alkyl group of any length, possibly substituted, an alkenyl group of any length, possibly substituted, an alkynyl group, possibly substituted, a cycloalkyl group, possibly substituted, or an aryl group, possi- In some embodiments of the disclosure, the catalytic system characterizing the process of the instant disclosure may comprise a base. In some embodiments, said base can be any conventional base. In some embodiments, non-limiting examples include: organic non-coordinating bases such as DBU, an alkaline or alkaline-earth metal carbonate, a carboxylate salt such as sodium or potassium acetate, or an alcoholate or hydroxide salt. Preferred bases are the alcoholate or hydroxide salts selected from the group consisting of the compounds of formula $(RO)_2M'$ and ROM", wherein M' is an alkaline-earth metal such as magnesium or calcium, M" is an alkaline metal such as sodium or potassium and R stands for hydrogen or a linear or branched alkyl group, wherein the alkyl group is as defined above.

The catalyst can be added to the reaction medium in a large range of concentrations. As non-limiting examples, one can cite as catalyst concentration values ranging from 0.001% to 50%, relative to the amount of substrate, thus representing respectively a substrate/catalyst (S/cat) ratio of 100,000 to 2. Preferably, the complex concentration will be comprised between 0.01% and 10%, i.e. a S/cat ratio of 10,000 to 10 respectively. In some preferred embodiments, there will be used concentrations in the range of 0.1 to 5%, corresponding to a S/cat ratio of 1,000 to 20 respectively.

If required, useful quantities of base, added to the reaction mixture, may be comprised in a relatively large range. In some embodiments, non-limiting examples include: ranges between 1 to 100 molar equivalents relative to the substrate. However, it should be noted that it is also possible to add a small amount of base (e.g. base/substrate=1 to 3) to achieve high yields.

In the processes of this disclosure, the catalytic reaction can be carried out in the presence or absence of a solvent. When a solvent is required or used for practical reasons, then any solvent currently used in catalytic reactions can be used for the purposes of the disclosure. Non-limiting examples include aromatic solvents such as benzene, toluene or xylene, hydrocarbon solvents such as hexane or cyclohexane, ethers such as tetrahydrofuran, or yet primary or secondary alcohols, or water, or mixtures thereof. A person skilled in the art is well able to select the solvent most convenient in each case to optimize the catalytic reaction.

The temperature at which the catalytic reaction can be carried out is comprised between −30° C. and 200° C., more preferably in the range of between 0° C. and 100° C. Of course, a person skilled in the art is also able to select the preferred temperature. Standard catalytic conditions, as used herein, typically implies the mixture of the substrate with the catalyst with or without a base, possibly in the presence of a solvent, and then treating such a mixture with the desired reactant at a chosen temperature in air or under an inert atmosphere of nitrogen or argon gas. Varying the reaction conditions, including for example, catalyst, temperature, solvent and reagent, to optimize the yield of the desired product would be well within the abilities of a person skilled in the art.

The present disclosure is described in the following Examples, which are set forth to aid in the understanding of the disclosure, and should not be construed to limit in any way the scope of the disclosure as defined in the claims which follow thereafter.

EXAMPLES

The disclosure will now be described in further details by way of the following examples, wherein the temperatures are indicated in degrees centigrade and the abbreviations have the usual meaning in the art.

All the procedures described hereafter have been carried out under an inert atmosphere unless stated otherwise. All preparations and manipulations under air-free conditions were carried out under $N_2$ or Ar atmospheres with the use of standard Schlenk, vacuum line and glove box techniques in dry, oxygen-free solvents. Deuterated solvents were degassed and dried over activated molecular sieves. NMR spectra were recorded on a 300 MHz spectrometer (300 MHz for $^1$H, 75 MHz for $^{13}$C and 121.5 MHz for $^{31}$P) or a 400 MHz spectrometer (400 MHz for $^1$H, 100 MHz for $^{13}$C and 162 MHz for $^{31}$P). All 31P chemical shifts were measured relative to 85% $H_3PO_4$ as an external reference. $^1$H and $^{13}$C chemical shifts were measured relative to partially deuterated solvent peaks but are reported relative to tetramethylsilane.

Example 1. Preparation of ethyl 4-(methyl-d3)cyclohex-3-ene-1-carboxylate

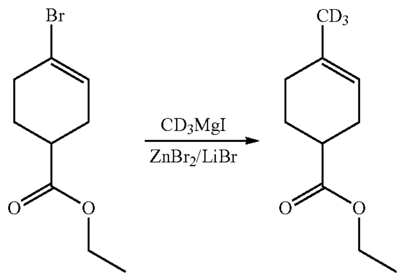

A solution of $CD_3MgI$ (228 ml of a 1.0 M solution in THF, 228 mmol) was added to a mixture of $ZnBr_2$ (51.4 g, 228 mmol) and LiBr (19.8 g, 228 mmol) at 0° C. and the mixture was allowed to warm to room temperature and stirred for 2 hours under argon. $PdCl_2$(dppf) (1.67 g, 2.28 mmol) was added followed by a solution of ethyl 4-bromocyclohex-3-enecarboxylate (53.15 g, 228 mmol) in THF (100 ml, slowly) and the mixture stirred at 60° C. for 48 hours under argon. It was quenched with water and ammonium chloride solution while maintaining room temperature. Diethyl ether (100 ml) was added and the phases were separated. The aqueous layer was extracted with diethyl ether (3×50 ml) and the combined organic layers were filtered through silica gel to remove the catalyst residue and dried ($MgSO_4$). The solvent was removed under reduced pressure to give the product as a pale-yellow liquid. Yield=37.1 g.

Example 2. Preparation of N-methoxy-N-methyl-4-(methyl-d3)cyclohex-3-ene-1-carboxamide

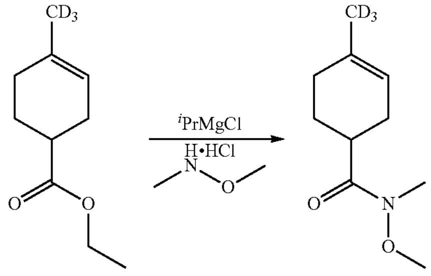

THF (250 ml) was added to a mixture of ethyl 4-(methyl-d3)cyclohex-3-ene-1-carboxylate (35 g, 204 mmol) and N,O-dimethylhydroxylamine hydrochloride (30.0 g, 307 mmol) and the mixture was cooled to −20° C. under argon. A solution of isopropylmagnesium chloride (307 ml of a 2.0 M solution in THF, 614 mmol) was added slowly and the mixture stirred for 2 hours at −20° C., then warmed to room temperature. After completion of the reaction (TLC), the mixture was quenched with ammonium chloride solution. Diethyl ether (250 ml) was added and the phases separated. The aqueous layer was extracted with diethyl ether (3×50 ml) and the combined organic phase was dried ($MgSO_4$) and filtered. The solvent was removed under reduced pressure to give the product as a pale-yellow liquid. Yield=37.24 g.

Example 3. Preparation of 1-(4-(methyl-d3)cyclohex-3-en-1-yl)ethan-1-one-2,2,2-d3

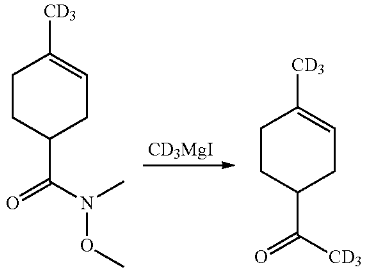

A solution of N-methoxy-N-methyl-4-(methyl-d3)cyclohex-3-ene-1-carboxamide (35 g, 188 mmol) in THF (300 ml) was cooled to −5° C. under argon. A solution of $CD_3MgI$ (197 ml of a 1.0 M solution in THF, 197 mmol) was added slowly and the mixture stirred for 2 hours at −5° C., then warmed to room temperature and stirred overnight. The mixture was quenched with ammonium chloride solution and diethyl ether (250 ml) was added and the phases separated. The aqueous layer was extracted with diethyl ether (3×50 ml) and the combined organic phase was dried ($MgSO_4$) and filtered. The solvent was removed under reduced pressure to give the product as a pale-yellow liquid. Yield=26.6 g.

Example 4. Preparation of 1-(methyl-d3)-4-(prop-1-en-2-yl-d5)cyclohex-1-ene

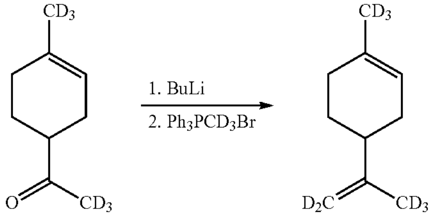

A solution of d3-methyltriphenylphosphonium bromide (93.6 g, 260 mmol) in THF (1000 ml) was cooled to 0° C. under argon. A solution of butyllithium (162.5 ml of a 1.6 M solution in hexanes, 260 mmol) was added slowly and the mixture stirred for 2 hours at 0° C. A solution of 1-(4-(methyl-d3)cyclohex-3-en-1-yl)ethan-1-one-2,2,2-d3 (25 g, 173 mmol) in THF (250 ml) was added and the mixture stirred for 1 hour at 0° C., then warmed to room temperature and stirred overnight. The mixture was quenched with ammonium chloride solution and diethyl ether (250 ml) was added and the phases separated. The aqueous layer was extracted with diethyl ether (3×50 ml) and the combined organic phase was dried ($MgSO_4$) and filtered. The solvent was removed under reduced pressure to give the product as a pale-yellow liquid. Yield=20.1 g.

Example 5. Preparation of N-methoxy-N,4-dimethylcyclohex-3-enecarbox-amide

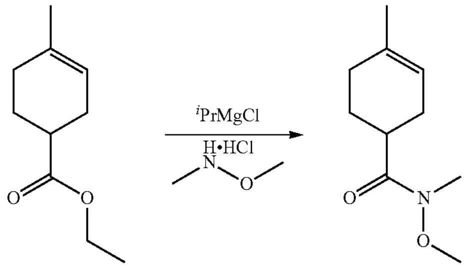

THF (250 ml) was added to a mixture of ethyl 4-(methyl)-cyclohex-3-enecarboxylate (34.32 g, 204 mmol) and N,O-dimethylhydroxylamine hydrochloride (30.0 g, 307 mmol) and the mixture was cooled to −20° C. under argon. A solution of isopropylmagnesium chloride (307 ml of a 2.0 M solution in THF, 614 mmol) was added slowly and the mixture stirred for 2 hours at −20° C., then warmed to room temperature. After completion of the reaction (TLC), the mixture was quenched with ammonium chloride solution. Diethyl ether (250 ml) was added and the phases separated. The aqueous layer was extracted with diethyl ether (3×50 ml) and the combined organic phase was dried ($MgSO_4$) and filtered. The solvent was removed under reduced pressure to give the product as a pale-yellow liquid. Yield=36.41 g.

Example 6. Preparation of 1-(4-methylcyclohex-3-en-1-yl)ethan-1-one-2,2,2-d3

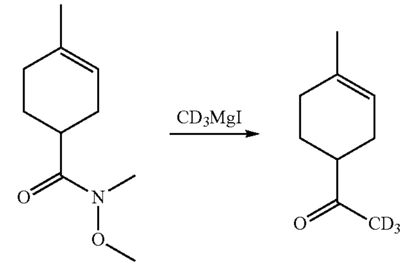

A solution of N-methoxy-N,4-dimethylcyclohex-3-en-ecarbox-amide (34.45 g, 188 mmol) in THF (300 ml) was cooled to −5° C. under argon. A solution of $CD_3MgI$ (197 ml of a 1.0 M solution in THF, 197 mmol) was added slowly and the mixture stirred for 2 hours at −5° C., then warmed to room temperature and stirred overnight. The mixture was quenched with ammonium chloride solution and diethyl ether (250 ml) was added and the phases separated. The aqueous layer was extracted with diethyl ether (3×50 ml) and the combined organic phase was dried ($MgSO_4$) and filtered. The solvent was removed under reduced pressure to give the product as a pale-yellow liquid. Yield=26.02 g.

Example 7. Preparation of 1-methyl-4-(prop-1-en-2-yl-d5)cyclohex-1-ene

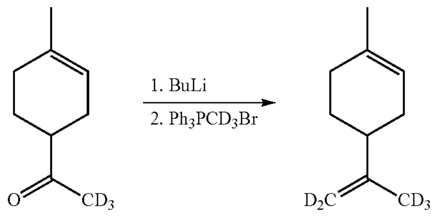

A solution of d3-methyltriphenylphosphonium bromide (93.6 g, 260 mmol) in THF (1000 ml) was cooled to 0° C. under argon. A solution of butyllithium (162.5 ml of a 1.6 M solution in hexanes, 260 mmol) was added slowly and the mixture stirred for 2 hours at 0° C. A solution of 1-(4-methylcyclohex-3-en-1-yl)ethan-1-one-2,2,2-d3 (24.43 g, 173 mmol) in THF (250 ml) was added and the mixture stirred for 1 hour at 0° C., then warmed to room temperature and stirred overnight. The mixture was quenched with ammonium chloride solution and diethyl ether (250 ml) was added and the phases separated. The aqueous layer was extracted with diethyl ether (3×50 ml) and the combined organic phase was dried ($MgSO_4$) and filtered. The solvent was removed under reduced pressure to give the product as a pale-yellow liquid. Yield=19.5 g.

Example 8. Preparation of 1-(4-(methyl-d3)cyclohex-3-en-1-yl)ethan-1-one

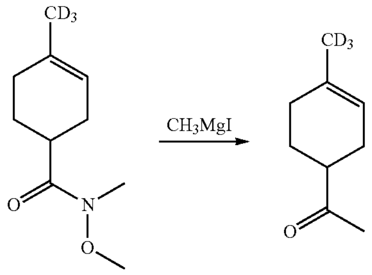 [SMILES: [2H]C([2H])([2H])C1=CCC(C(=O)N(C)OC)CC1 ; "CH3MgI" ; [2H]C([2H])([2H])C1=CCC(C(C)=O)CC1]

A solution of N-methoxy-N-methyl-4-(methyl-d3)cyclohex-3-ene-1-carboxamide (35 g, 188 mmol) in THF (300 ml) was cooled to −5° C. under argon. A solution of $CH_3MgI$ (197 ml of a 1.0 M solution in THF, 197 mmol) was added slowly and the mixture stirred for 2 hours at −5° C., then warmed to room temperature and stirred overnight. The mixture was quenched with ammonium chloride solution and diethyl ether (250 ml) was added and the phases separated. The aqueous layer was extracted with diethyl ether (3×50 ml) and the combined organic phase was dried ($MgSO_4$) and filtered. The solvent was removed under reduced pressure to give the product as a pale-yellow liquid. Yield=27.2 g.

Example 9. Preparation of 1-(methyl-d3)-4-(prop-1-en-2-yl)cyclohex-1-ene

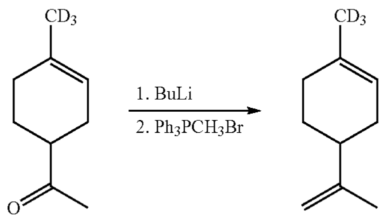

A solution of methyltriphenylphosphonium bromide (93.0 g, 260 mmol) in THF (1000 ml) was cooled to 0° C. under argon. A solution of butyllithium (162.5 ml of a 1.6 M solution in hexanes, 260 mmol) was added slowly and the mixture stirred for 2 hours at 0° C. A solution of 1-(4-(methyl-d3)cyclohex-3-en-1-yl)ethan-1-one (24.4 g, 173 mmol) in THF (250 ml) was added and the mixture stirred for 1 hour at 0° C., then warmed to room temperature and stirred overnight. The mixture was quenched with ammonium chloride solution and diethyl ether (250 ml) was added and the phases separated. The aqueous layer was extracted with diethyl ether (3×50 ml) and the combined organic phase was dried ($MgSO_4$) and filtered. The solvent was removed under reduced pressure to give the product as a pale-yellow liquid. Yield=20.1 g.

Example 10. Preparation of methyl 4-methylcyclohex-3-enecarboxylate

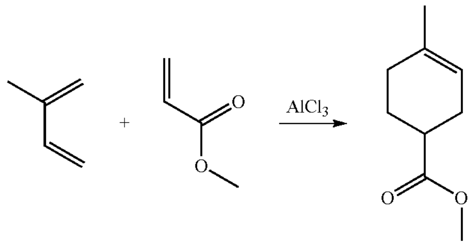

A solution of isoprene (15.0 g, 220 mmol) and methyl acrylate (19.0 g, 220 mmol) in diethyl ether (200 ml) was cooled to −78° C. and $AlCl_3$ (2.9 g, 22 mmol) was added with stirring under argon. The mixture was allowed to warm to room temperature and stirred overnight. Water (50 ml) was added to quench the reaction. The mixture was extracted with ether (3×20 ml) and the combined organic portion was washed with brine, dried ($MgSO_4$) and the ether was removed under reduced pressure to give the product as a colourless oil. Yield=34.5 g.

Example 11. Preparation of 4-methylcyclohex-3-enecarboxylic acid

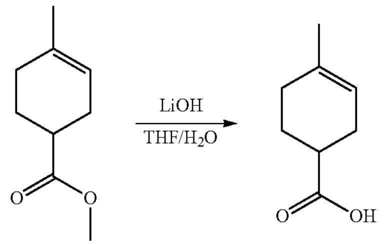

Methyl 4-methylcyclohex-3-ene-1-carboxylate (10.0 g, 64.8 mmol) was dissolved in a 10:1 mixture of THF/water (65 ml) and LiOH (6.66 g, 0.278 mol) added. The mixture was stirred overnight at room temperature. The THF was removed under reduced pressure and 1M NaOH solution (50 ml) added. Dilute sulfuric acid (1M) was added until the solution was acidic. The mixture was cooled to room temperature and extracted with diethyl ether (3×20 ml). The organic fraction was dried ($Na_2SO_4$) and the solvent removed under reduced pressure to give the product as a colourless, crystalline solid. Yield=7.0 g.

Example 12. Resolution of 4-methylcyclohex-3-enecarboxylic acid

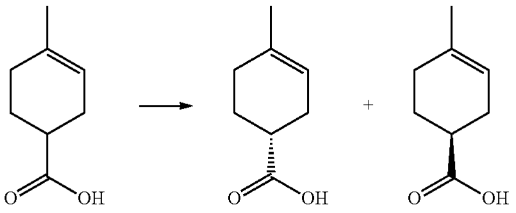

4-methylcyclohex-3-enecarboxylic acid was resolved using brucine and strychnine as described by Fisher and Perkin (J. Chem. Soc. 1908, 93, 1871-1876).

Example 13. Preparation of (R)-4-(methyl-d3)cyclohex-3-ene-1-carboxylic acid and (S)-4-(methyl-d3)cyclohex-3-ene-1-carboxylic acid

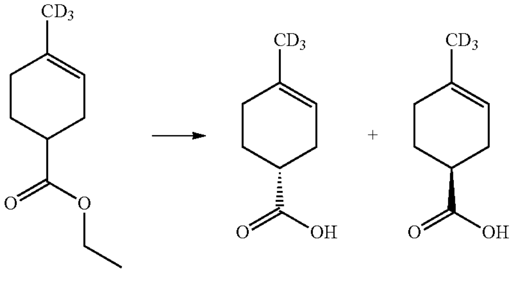

(R)-4-(Methyl-d3)cyclohex-3-ene-1-carboxylic acid and (S)-4-(methyl-d3)cyclohex-3-ene-1-carboxylic acid were prepared from racemic ethyl 4-(methyl-d3)cyclohex-3-ene-1-carboxylate using the procedure described in Examples 11 and 12.

Example 14. Preparation of (R)-1-(methyl-d3)-4-(prop-1-en-2-yl-d5)cyclohex-1-ene

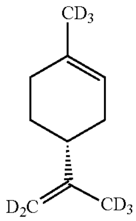

(R)-1-(Methyl-d3)-4-(prop-1-en-2-yl-d5)cyclohex-1-ene was prepared from (R)-4-(methyl-d3)cyclohex-3-ene-1-carboxylic acid using the procedures described in Examples 2 to 4.

Example 15. Preparation of (R)-1-methyl-4-(prop-1-en-2-yl-d5)cyclohex-1-ene

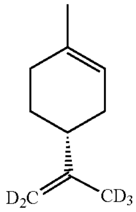

(R)-1-Methyl-4-(prop-1-en-2-yl-d5)cyclohex-1-ene was prepared from (R)-(4-methylcyclohex-3-enecarboxylic acid) using the procedures described in Examples 5 to 7.

Example 16. Preparation of (R)-1-(methyl-d3)-4-(prop-1-en-2-yl)cyclohex-1-ene

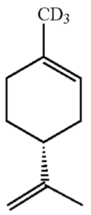

(R)-1-(Methyl-d3)-4-(prop-1-en-2-yl)cyclohex-1-ene was prepared from (R)-4-(methyl-d3)cyclohex-3-ene-1-carboxylic acid using the procedures described in Examples 8 to 9.

Example 17. Preparation of (1S,2S,4R)-2-bromo-1-methyl-4-(prop-1-en-2-yl)cyclohexanol

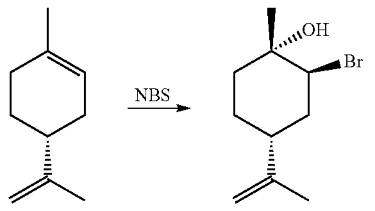

(R)-(+)-Limonene (25 g, 183 m mol) was dissolved in a mixture of water (50 ml) and acetone (200 ml) and cooled to 0° C. NBS (37.5 g, 210 mmol) was dissolved in acetone (350 ml) and added slowly over approximately 40 minutes. Once addition of the NBS solution was complete the ice bath was removed, and the mixture was stirred until completed (TLC). The acetone was removed under reduced pressure and the mixture was quenched with sodium bicarbonate solution. The mixture was extracted with ether (3x30 ml) and the combined ether fraction washed with water (3x50 ml) and dried with sodium sulfate. The solvent was removed under reduced pressure and the bromohydrin was used for the next step without purification. Yield=42.2 g.

Example 18. Preparation of (1S,4R,6R)-1-methyl-4-(prop-1-en-2-yl)-7-oxabicyclo[4.1.0]heptane

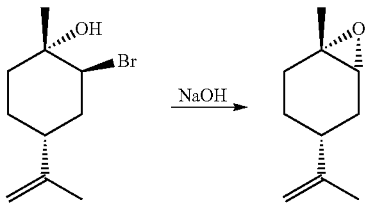

The bromohydrin from Example 16 was added to a round bottom flask and 6M NaOH (50 ml) was added and the mixture heated to 60° C. for 2 hours and vigorous stirring. After cooling to room temperature, the layers were separated, and the organic layer was dissolved in ether (60 ml) and washed with saturated sodium bicarbonate (45 ml) and then water (45 ml) and dried ($Na_2SO_4$). The mixture was filtered, and the solvent was removed under reduced pressure. Yield=27.2 g.

Example 19. Preparation of (1S,2S,4R)-2-(dimethylamino)-1-methyl-4-(prop-1-en-2-yl)cyclohexanol

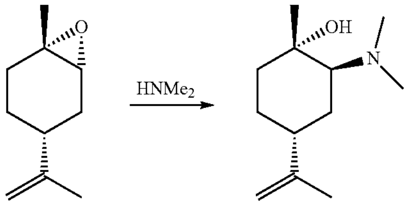

The trans-Limonene oxide (27 g, 177 mmol) from above and dimethylamine (40 g of a 40% solution in water, 350 mmol) were added to a 100 ml Parr pressure reactor and heated at 100° C. for 18 hours. The mixture was cooled to room temperature and the volatiles were removed under reduced pressure. The mixture was extracted using diethyl ether (2x25 ml). The organic fraction was dried ($Na_2SO_4$), filtered and the solvent removed under reduced pressure. Yield=28.5 g.

Example 20. Preparation of (1S,2S,5R)-2-hydroxy-N,N,2-trimethyl-5-(prop-1-en-2-yl)cyclohexanamine oxide

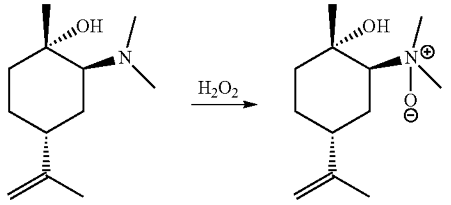

A solution of hydrogen peroxide (45 g of a 30% solution in water, 397 mmol) was slowly added to solution of the aminoalcohol (60.0 g, 303 mmol) in ethanol (120 ml) and the mixture heated to reflux for 2.5 hrs. It was cooled to room temperature and sodium sulfite (13.0 g, 103 mmol) in water (45 ml) added. The mixture was stirred until no peroxide was detected using a peroxide test strip. Acetone (80 ml) was added to precipitate the salts. The mixture was filtered, and the filtrate washed with acetone (15 ml). The combined filtrate was concentrated under reduced pressure to give the product. The NMR showed quantitative conversion of the aminoalcohol to the oxide. It contained ethanol, water and acetone residues and was used in the next step without further purification.

Example 21. Preparation of (1S,4R)-1-methyl-4-(prop-1-en-2-yl)cyclohex-2-enol

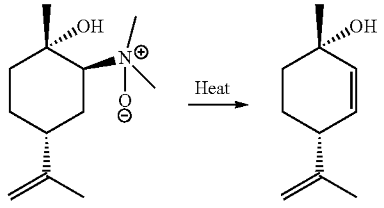

The amine oxide from above was distilled under vacuum and the distillate collected into a cold trap. Product formation commenced occurred between 150° C. and 162° C. to give a pale-yellow oil. This was dissolved in ether (100 ml) and washed with 1M $H_2SO_4$ (2x100 ml), then $NaHCO_3$ solution. The organic fraction was separated, dried and the solvent removed under reduced pressure. Yield=38.2 g.

Example 22. Preparation of (1S,4R)-1-(methyl-d3)-4-(prop-1-en-2-yl-d5)cyclohex-2-en-1-ol

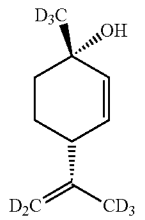

This was prepared from (R)-1-(Methyl-d3)-4-(prop-1-en-2-yl-d5)cyclohex-1-ene using the procedures described in Examples 17 to 21.

Example 23. Preparation of (1S,4R)-1-methyl-4-(prop-1-en-2-yl-d5)cyclohex-2-en-1-ol

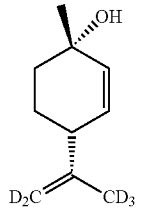

This was prepared from (R)-1-methyl-4-(prop-1-en-2-yl-d5)cyclohex-1-ene using the procedures described in Examples 17 to 21.

Example 24. Preparation of (1S,4R)-1-(methyl-d3)-4-(prop-1-en-2-yl)cyclohex-2-en-1-ol

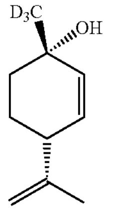

This was prepared from (R)-1-(Methyl-d3)-4-(prop-1-en-2-yl)cyclohex-1-ene using the procedures described in Examples 17 to 21.

Example 25. Preparation of (1'R,2'R)-5'-(methyl-d3)-2'-(prop-1-en-2-yl-d5)-1',2',3',4'-tetrahydro-[1,1'-biphenyl]-2,4,6-triol

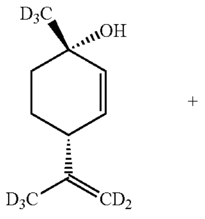

-continued

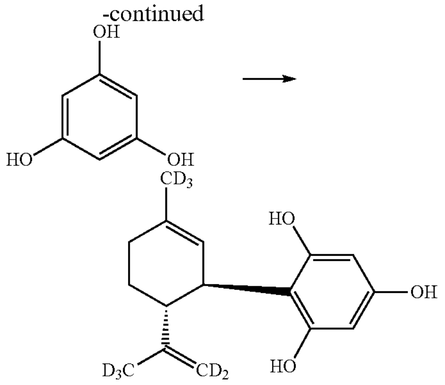

Anhydrous ethanol (60 ml) were added to a mixture of 1,3,5-trihydroxybenzene (12.42 g, 98.5 mmol) and anhydrous magnesium sulfate (10 g) and the suspension was cooled to 0° C. A solution of tetrafluoroboric acid diethyl ether (2.13 g, 13.1 mmol) in dichloromethane (10 ml) was added slowly with stirring. A solution of (1S,4R)-1-(methyl-d3)-4-(prop-1-en-2-yl-d5)cyclohex-2-en-1-ol (10.53 g, 65.7 mmol) in dichloromethane (100 ml) was added slowly over 30 minutes at 0° C. with stirring. The mixture was allowed to warm to room temperature and stirred for 15 hours. The reaction mixture was filtered and the filtrate was quenched with saturated sodium bicarbonate solution and the phases were separated. The organic layer was extracted with water (2×100 ml) and dried ($MgSO_4$). It was filtered and the solvent was removed under reduced pressure to give a viscous, sticky residue. This was chromatographed using hexanes/ethyl acetate to give the product as a viscous, pale-yellow oil. Yield=15.2 grams.

Example 26. Preparation of (1'R,2'R)-2,6-dihydroxy-5'-(methyl-d3)-2'-(prop-1-en-2-yl-d5)-1',2',3',4'-tetrahydro-[1,1'-biphenyl]-4-yl trifluoromethanesulfonate

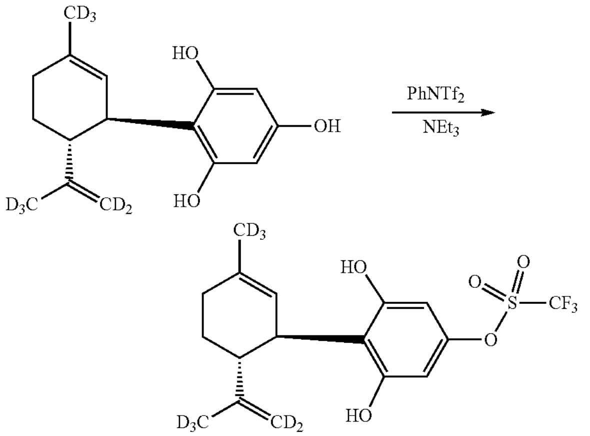

Triethylamine (14.2 g, 167 mmol) was added to a solution of (1'R,2'R)-5'-(methyl-d3)-2'-(prop-1-en-2-yl-d5)-1',2',3',4'-tetrahydro-[1,1'-biphenyl]-2,4,6-triol (15.0 g, 55.9 mmol) in dichloromethane (150 ml) and the mixture was cooled to 0° C. A solution of N-Phenyl-bis(trifluoromethanesulfonimide) (20.13 g, 56.4 mmol) was added slowly and the mixture allowed to warm to room temperature and stirred overnight.

The reaction was quenched with water and the phases separated. The aqueous layer was extracted with dichloromethane (3×50 ml) and the combined organic layers washed with brine and dried ($MgSO_4$). It was filtered through a pad of silica gel and the solvent removed under reduced pressure. The crude residue was chromatographed using hexanes/EA (6:1) and the pure product was isolated as a pale-yellow oil. Yield=17.4 grams.

Example 27. Preparation of (1'R,2'R)-5'-(methyl-d3)-2'-(prop-1-en-2-yl-d5)-2,6-bis((trimethylsilyl)oxy)-1',2',3',4'-tetrahydro-[1,1'-biphenyl]-4-yl trifluoromethanesulfonate

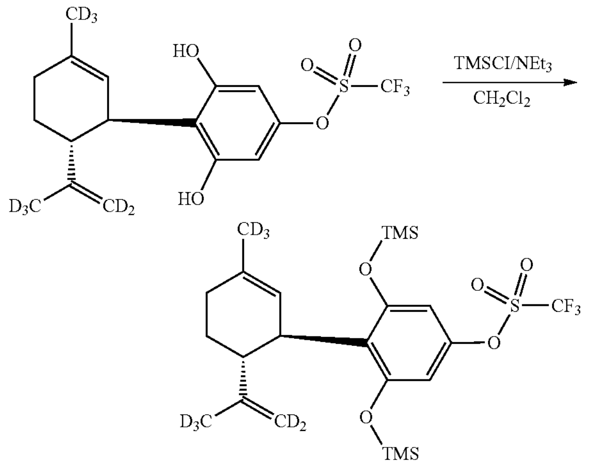

TMSCl (9.97 g, 91.75 mmol) was added to a mixture of (1'R,2'R)-2,6-dihydroxy-5'-(methyl-d3)-2'-(prop-1-en-2-yl-d5)-1',2',3',4'-tetrahydro-[1,1'-biphenyl]-4-yl trifluoromethanesulfonate (10.21 g, 25.5 mmol) and NEt3 (9.26 g, 91.7 mmol) in $CH_2C_{12}$ (60 ml) at room temperature (water bath) under argon. The mixture was stirred at room temperature for 15 hours. It was filtered and the solvent was removed from the filtrate. It was then suspended in hexanes/ethyl acetate (1:1, 80 ml) and stirred for 30 minutes hours. It was filtered and the solvent removed under reduced pressure and the product dried under vacuum to give a pale-brown oil. Yield=13.42 g.

Example 28. Preparation of (1'R,2'R)-5'-methyl-2'-(prop-1-en-2-yl-d5)-1',2',3',4'-tetrahydro-[1,1'-biphenyl]-2,4,6-triol

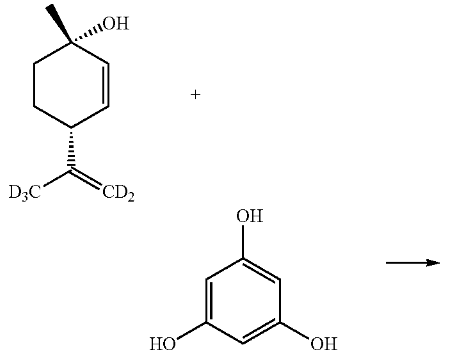

-continued

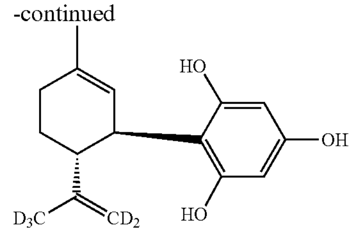

Anhydrous ethanol (60 ml) were added to a mixture of 1,3,5-trihydroxybenzene (12.42 g, 98.5 mmol) and anhydrous magnesium sulfate (10 g) and the suspension was cooled to 0° C. A solution of tetrafluoroboric acid diethyl ether (2.13 g, 13.1 mmol) in dichloromethane (10 ml) was added slowly with stirring. A solution of (1S,4R)-1-methyl-4-(prop-1-en-2-yl-d5)cyclohex-2-en-1-ol (10.33 g, 65.7 mmol) in dichloromethane (100 ml) was added slowly over 30 minutes at 0° C. with stirring. The mixture was allowed to warm to room temperature and stirred for 15 hours. The reaction mixture was filtered and the filtrate was quenched with saturated sodium bicarbonate solution and the phases were separated. The organic layer was extracted with water (2×100 ml) and dried ($MgSO_4$). It was filtered and the solvent was removed under reduced pressure to give a viscous, sticky residue. This was chromatographed using hexanes/ethyl acetate to give the product as a viscous, pale-yellow oil. Yield=14.8 grams.

Example 29. Preparation of (1'R,2'R)-2,6-dihydroxy-5'-methyl-2'-(prop-1-en-2-yl-d5)-1',2',3',4'-tetrahydro-[1,1'-biphenyl]-4-yl trifluoromethanesulfonate

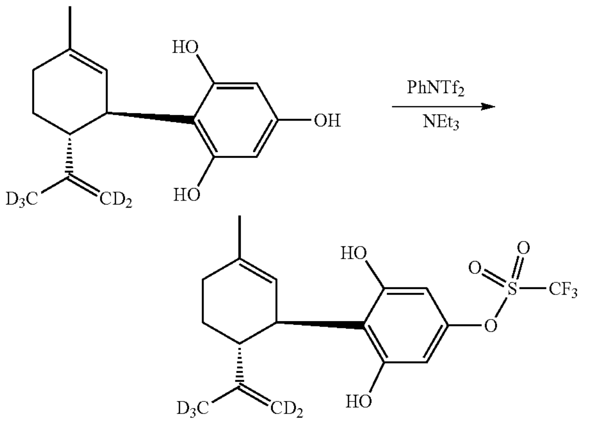

Triethylamine (14.2 g, 167 mmol) was added to a solution of (1'R,2'R)-5'-methyl-2'-(prop-1-en-2-yl-d5)-1',2',3',4'-tetrahydro-[1,1'-biphenyl]-2,4,6-triol (14.83 g, 55.9 mmol) in dichloromethane (150 ml) and the mixture was cooled to 0° C. A solution of N-Phenyl-bis(trifluoromethanesulfonimide) (20.13 g, 56.4 mmol) was added slowly and the mixture allowed to warm to room temperature and stirred overnight. The reaction was quenched with water and the phases separated. The aqueous layer was extracted with dichloromethane (3×50 ml) and the combined organic layers washed with brine and dried ($MgSO_4$). It was filtered through a pad of silica gel and the solvent removed under reduced pressure. The crude residue was chromatographed using hexanes/EA (6:1) and the pure product was isolated as a pale-yellow oil. Yield=16.7 grams.

Example 30. Preparation of (1'R,2'R)-5'-methyl-2'-(prop-1-en-2-yl-d5)-2,6-bis((trimethylsilyl)oxy)-1',2',3',4'-tetrahydro-[1,1'-biphenyl]-4-yl trifluoromethanesulfonate

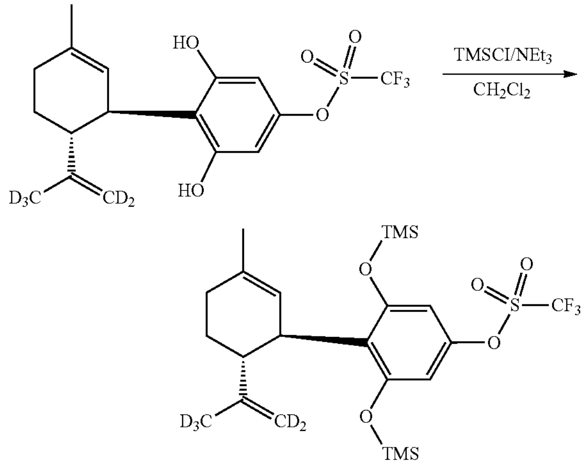

TMSCl (9.97 g, 91.75 mmol) was added to a mixture of (1'R,2'R)-2,6-dihydroxy-5'-methyl-2'-(prop-1-en-2-yl-d5)-1',2',3',4'-tetrahydro-[1,1'-biphenyl]-4-yl trifluoromethanesulfonate (10.13 g, 25.5 mmol) and NEt3 (9.26 g, 91.7 mmol) in $CH_2Cl_2$ (60 ml) at room temperature (water bath) under argon. The mixture was stirred at room temperature for 15 hours. It was filtered and the solvent was removed from the filtrate. It was then suspended in hexanes/ethyl acetate (1:1, 80 ml) and stirred for 30 minutes hours. It was filtered and the solvent removed under reduced pressure and the product dried under vacuum to give a pale-brown oil. Yield=12.80 g.

Example 31. Preparation of (1'R,2'R)-5'-(methyl-d3)-2'-(prop-1-en-2-yl)-1',2',3',4'-tetrahydro-[1,1'-biphenyl]-2,4,6-triol

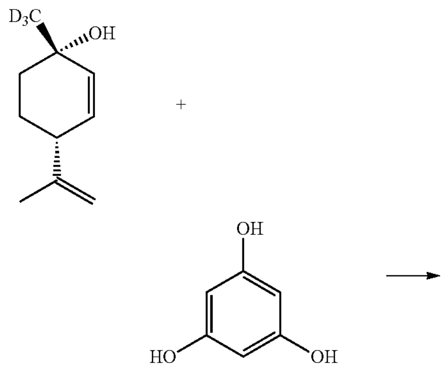

-continued

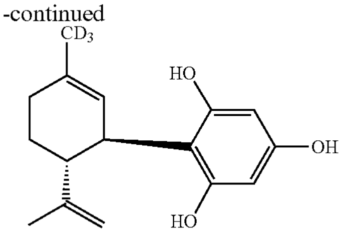

Anhydrous ethanol (60 ml) were added to a mixture of 1,3,5-trihydroxybenzene (12.42 g, 98.5 mmol) and anhydrous magnesium sulfate (10 g) and the suspension was cooled to 0° C. A solution of tetrafluoroboric acid diethyl ether (2.13 g, 13.1 mmol) in dichloromethane (10 ml) was added slowly with stirring. A solution of (1S,4R)-1-(methyl-d3)-4-(prop-1-en-2-yl)cyclohex-2-en-1-ol (10.20 g, 65.7 mmol) in dichloromethane (100 ml) was added slowly over 30 minutes at 0° C. with stirring. The mixture was allowed to warm to room temperature and stirred for 15 hours. The reaction mixture was filtered, and the filtrate was quenched with saturated sodium bicarbonate solution and the phases were separated. The organic layer was extracted with water (2×100 ml) and dried ($MgSO_4$). It was filtered and the solvent was removed under reduced pressure to give a viscous, sticky residue. This was chromatographed using hexanes/ethyl acetate to give the product as a viscous, pale-yellow oil. Yield=14.3 grams.

Example 32. Preparation of (1'R,2'R)-2,6-dihydroxy-5'-(methyl-d3)-2'-(prop-1-en-2-yl)-1',2',3',4'-tetrahydro[1,1'-biphenyl]-4-yl trifluoromethanesulfonate

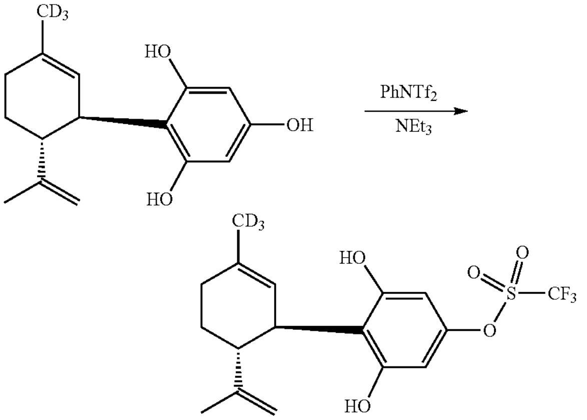

Triethylamine (14.2 g, 167 mmol) was added to a solution of (1'R,2'R)-5'-(methyl-d3)-2'-(prop-1-en-2-yl)-1',2',3',4'-tetrahydro-[1,1'-biphenyl]-2,4,6-triol (14.72 g, 55.9 mmol) in dichloromethane (150 ml) and the mixture was cooled to 0° C. A solution of N-Phenyl-bis(trifluoromethanesulfonimide) (20.13 g, 56.4 mmol) was added slowly and the mixture allowed to warm to room temperature and stirred overnight. The reaction was quenched with water and the phases separated. The aqueous layer was extracted with dichloromethane (3×50 ml) and the combined organic layers washed with brine and dried ($MgSO_4$). It was filtered through a pad of silica gel and the solvent removed under reduced pressure. The crude residue was chromatographed using hexanes/EA (6:1) and the pure product was isolated as a pale-yellow oil. Yield=16.2 grams.

Example 33. Preparation of (1'R,2'R)-5'-(methyl-d3)-2'-(prop-1-en-2-yl)-2,6-bis((trimethylsilyl)oxy)-1',2',3',4'-tetrahydro-[1,1'-biphenyl]-4-yl trifluoromethanesulfonate

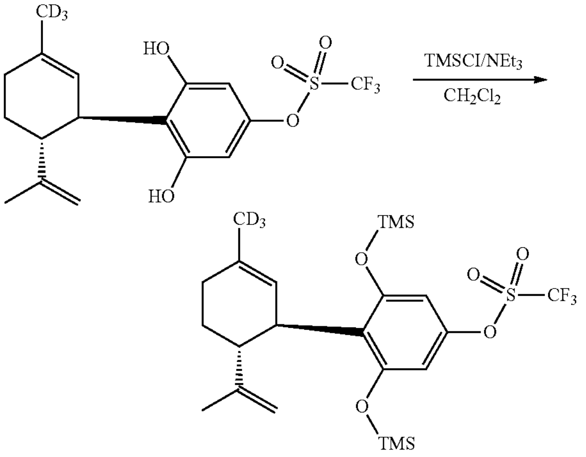

TMSCI (9.97 g, 91.75 mmol) was added to a mixture of (1'R,2'R)-2,6-dihydroxy-5'-(methyl-d3)-2'-(prop-1-en-2-yl)-1',2',3',4'-tetrahydro-[1,1'-biphenyl]-4-yl trifluoromethanesulfonate (10.08 g, 25.5 mmol) and NEt3 (9.26 g, 91.7 mmol) in $CH_2C_{12}$ (60 ml) at room temperature (water bath) under argon. The mixture was stirred at room temperature for 15 hours. It was filtered and the solvent was removed from the filtrate. It was then suspended in hexanes/ethyl acetate (1:1, 80 ml) and stirred for 30 minutes hours. It was filtered and the solvent removed under reduced pressure and the product dried under vacuum to give a pale-brown oil. Yield=12.63 g.

Example 34. Reaction of (1'R,2'R)-5'-(methyl-d3)-2'-(prop-1-en-2-yl-d5)-2,6-bis((trimethylsilyl)oxy)-1',2',3',4'-tetrahydro-[1,1'-biphenyl]-4-yl trifluoromethanesulfonate with n pentylzinc bromide

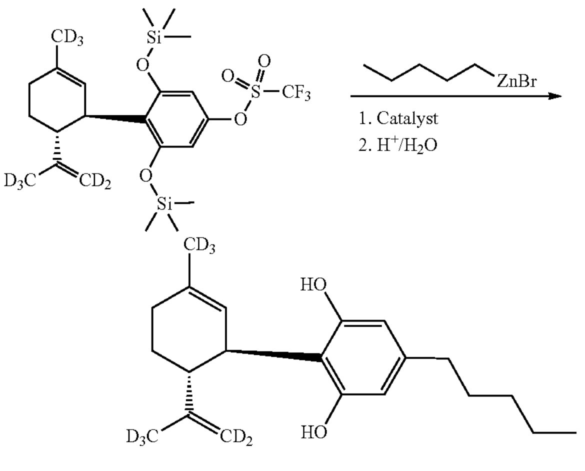

A solution of n-pentylzinc bromide (5.6 ml of a 0.5 M solution in THF, 2.80 mmol) was added to a mixture of (1'R,2'R)-5'-(methyl-d3)-2'-(prop-1-en-2-yl-d5)-2,6-bis((trimethylsilyl)oxy)-1',2',3',4'-tetrahydro-[1,1'-biphenyl]-4-yl trifluoromethanesulfonate (1.02 g, 1.87 mmol) and $PdCl_2$ (dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3×10 ml) and the combined extracts dried ($MgSO_4$) then evaporated to dryness. The product was purified by flash chromatography using hexanes/ethylacetate. Yield=0.58 g.

Example 35. Reaction of (1'R,2'R)-5'-(methyl-d3)-2'-(prop-1-en-2-yl-d5)-2,6-bis((trimethylsilyl)oxy)-1',2',3',4'-tetrahydro-[1,1'-biphenyl]-4-yl trifluoromethanesulfonate with n propylzinc bromide

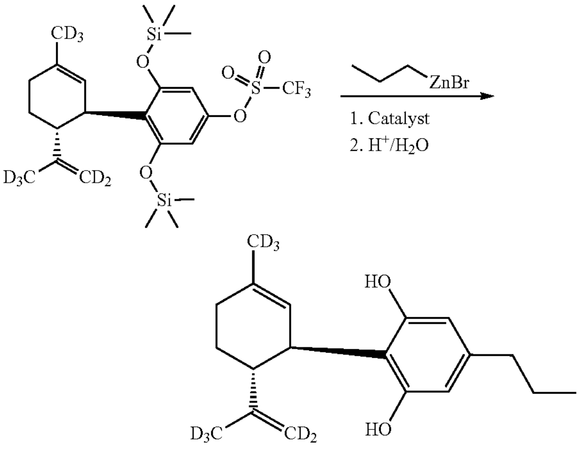

A solution of n-propylzinc bromide (5.6 ml of a 0.5 M solution in THF, 2.80 mmol) was added to a mixture of (1'R,2'R)-5'-(methyl-d3)-2'-(prop-1-en-2-yl-d5)-2,6-bis((trimethylsilyl)oxy)-1',2',3',4'-tetrahydro-[1,1'-biphenyl]-4-yl trifluoromethanesulfonate (1.02 g, 1.87 mmol) and $PdCl_2$ (dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3×10 ml) and the combined extracts dried ($MgSO_4$) then evaporated to dryness. The product was purified by flash chromatography using hexanes/ethylacetate. Yield=0.54 g.

Example 36. Reaction of (1'R,2'R)-5'-(methyl-d3)-2'-(prop-1-en-2-yl-d5)-2,6-bis((trimethylsilyl)oxy)-1',2',3',4'-tetrahydro-[1,1'-biphenyl]-4-yl trifluoromethanesulfonate with phenethylzinc bromide

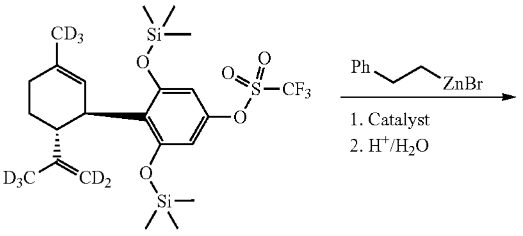

-continued

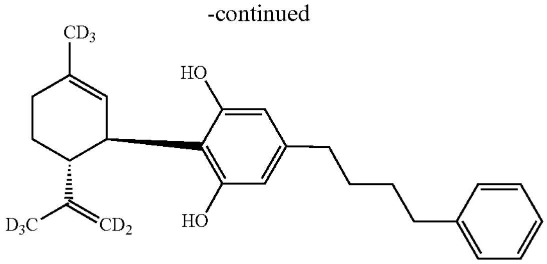

A solution of phenethylzinc bromide (5.6 ml of a 0.5 M solution in THF, 2.80 mmol) was added to a mixture of (1'R,2'R)-5'-(methyl-d3)-2'-(prop-1-en-2-yl-d5)-2,6-bis ((trimethylsilyl)oxy)-1',2',3',4'-tetrahydro-[1,1'-biphenyl]-4-yl trifluoromethanesulfonate (1.02 g, 1.87 mmol) and $PdCl_2$ (dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3x10 ml) and the combined extracts dried ($MgSO_4$) then evaporated to dryness. The product was purified by flash chromatography using hexanes/ethylacetate. Yield=0.62 g.

Example 37. Reaction of (1'R,2'R)-5'-methyl-2'-(prop-1-en-2-yl-d5)-2,6-bis((trimethylsilyl)oxy)-1',2',3',4'-tetrahydro-[1,1'-biphenyl]-4-yl trifluoromethanesulfonate with n pentylzinc bromide

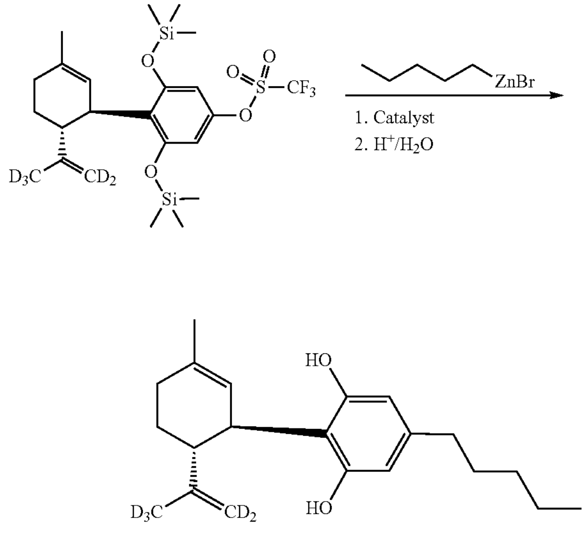

A solution of n-pentylzinc bromide (5.6 ml of a 0.5 M solution in THF, 2.80 mmol) was added to a mixture of (1'R,2'R)-5'-methyl-2'-(prop-1-en-2-yl-d5)-2,6-bis((trimethylsilyl)oxy)-1',2',3',4'-tetrahydro-[1,1'-biphenyl]-4-yl trifluoromethanesulfonate (1.01 g, 1.87 mmol) and $PdCl_2$(dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3x10 ml) and the combined extracts dried ($MgSO_4$) then evaporated to dryness. The product was purified by flash chromatography using hexanes/ethylacetate. Yield=0.57 g.

Example 38. Reaction of (1'R,2'R)-5'-methyl-2'-(prop-1-en-2-yl-d5)-2,6-bis((trimethylsilyl)oxy)-1',2',3',4'-tetrahydro-[1,1'-biphenyl]-4-yl trifluoromethanesulfonate with n propylzinc bromide

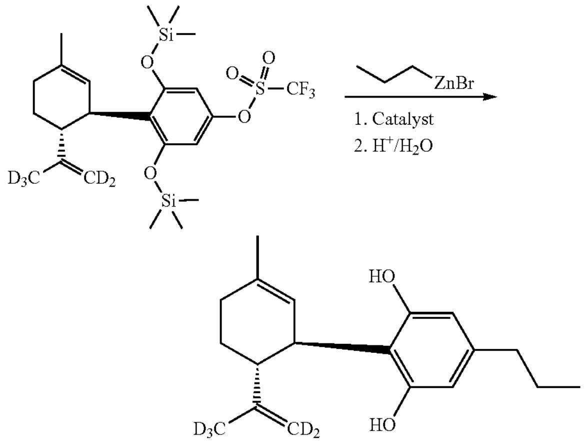

A solution of n-propylzinc bromide (5.6 ml of a 0.5 M solution in THF, 2.80 mmol) was added to a mixture of (1'R,2'R)-5'-methyl-2'-(prop-1-en-2-yl-d5)-2,6-bis((trimethylsilyl)oxy)-1',2',3',4'-tetrahydro-[1,1'-biphenyl]-4-yl trifluoromethanesulfonate (1.01 g, 1.87 mmol) and $PdCl_2$(dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3x10 ml) and the combined extracts dried ($MgSO_4$) then evaporated to dryness. The product was purified by flash chromatography using hexanes/ethylacetate. Yield=0.52 g.

Example 39. Reaction of (1'R,2'R)-5'-methyl-2'-(prop-1-en-2-yl-d5)-2,6-bis((trimethylsilyl)oxy)-1',2',3',4'-tetrahydro-[1,1'-biphenyl]-4-yl trifluoromethanesulfonate with phenethylzinc bromide

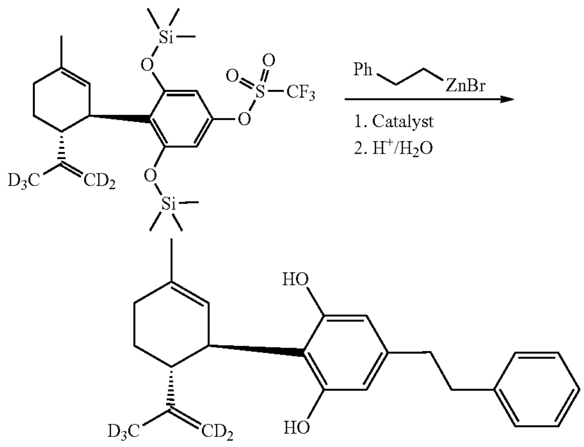

A solution of phenethylzinc bromide (5.6 ml of a 0.5 M solution in THF, 2.80 mmol) was added to a mixture of (1'R,2'R)-5'-methyl-2'-(prop-1-en-2-yl-d5)-2,6-bis((trimethylsilyl)oxy)-1',2',3',4'-tetrahydro-[1,1'-biphenyl]-4-yl trifluoromethanesulfonate (1.01 g, 1.87 mmol) and $PdCl_2$(dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3×10 ml) and the combined extracts dried ($MgSO_4$) then evaporated to dryness. The product was purified by flash chromatography using hexanes/ethylacetate. Yield=0.63 g.

Example 40. Reaction of (1'R,2'R)-5'-(methyl-d3)-2'-(prop-1-en-2-yl)-2,6-bis((trimethylsilyl)oxy)-1',2',3',4'-tetrahydro-[1,1'-biphenyl]-4-yl trifluoromethanesulfonate with n pentylzinc bromide

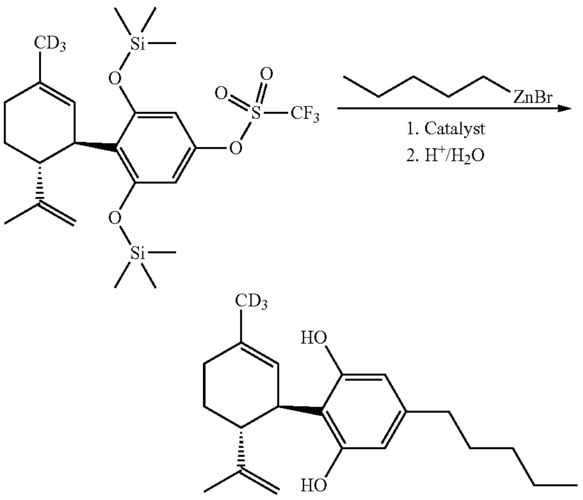

A solution of n-pentylzinc bromide (5.6 ml of a 0.5 M solution in THF, 2.80 mmol) was added to a mixture of (1'R,2'R)-5'-(methyl-d3)-2'-(prop-1-en-2-yl)-2,6-bis((trimethylsilyl)oxy)-1',2',3',4'-tetrahydro-[1,1'-biphenyl]-4-yl trifluoromethanesulfonate (1.01 g, 1.87 mmol) and $PdCl_2$ (dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3×10 ml) and the combined extracts dried ($MgSO_4$) then evaporated to dryness. The product was purified by flash chromatography using hexanes/ethylacetate. Yield=0.58 g.

Example 41. Reaction of (1'R,2'R)-5'-(methyl-d3)-2'-(prop-1-en-2-yl)-2,6-bis((trimethylsilyl)oxy)-1',2',3',4'-tetrahydro-[1,1'-biphenyl]-4-yl trifluoromethanesulfonate with n propylzinc bromide

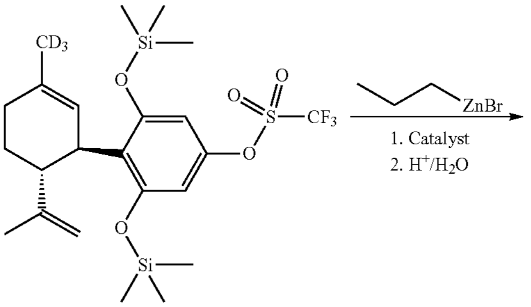

-continued

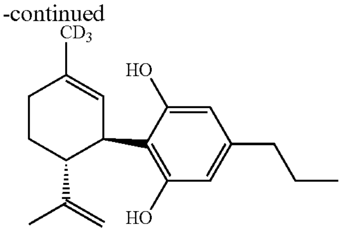

A solution of n-propylzinc bromide (5.6 ml of a 0.5 M solution in THF, 2.80 mmol) was added to a mixture of (1'R,2'R)-5'-(methyl-d3)-2'-(prop-1-en-2-yl)-2,6-bis((trimethylsilyl)oxy)-1',2',3',4'-tetrahydro-[1,1'-biphenyl]-4-yl trifluoromethanesulfonate (1.01 g, 1.87 mmol) and $PdCl_2$ (dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3×10 ml) and the combined extracts dried ($MgSO_4$) then evaporated to dryness. The product was purified by flash chromatography using hexanes/ethylacetate. Yield=0.53 g.

Example 42. Reaction of (1'R,2'R)-5'-(methyl-d3)-2'-(prop-1-en-2-yl)-2,6-bis((trimethylsilyl)oxy)-1',2',3',4'-tetrahydro-[1,1'-biphenyl]-4-yl trifluoromethanesulfonate with phenethylzinc bromide

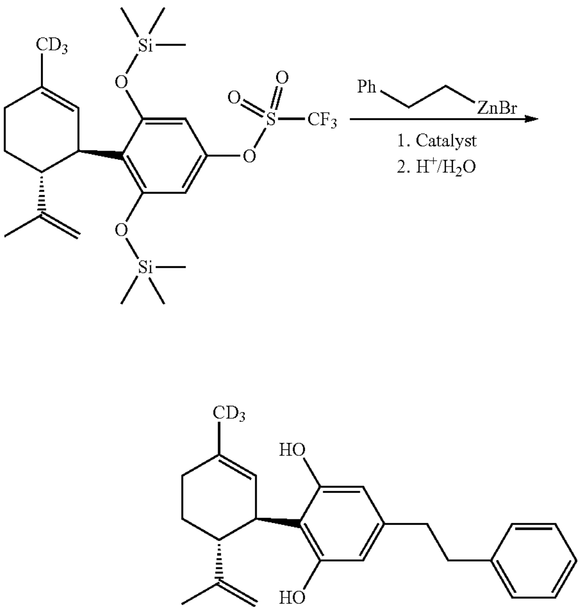

A solution of phenethylzinc bromide (5.6 ml of a 0.5 M solution in THF, 2.80 mmol) was added to a mixture of (1'R,2'R)-5'-(methyl-d3)-2'-(prop-1-en-2-yl)-2,6-bis((trimethylsilyl)oxy)-1',2',3',4'-tetrahydro-[1,1'-biphenyl]-4-yl trifluoromethanesulfonate (1.01 g, 1.87 mmol) and $PdCl_2$ (dppf) (34 mg, 0.047 mmol, 2.5%) and the mixture stirred at room temperature for 2 hours under argon. Dilute $H_2SO_4$ (2 ml of a 2M solution) was added and the mixture stirred for 1 hour at room temperature. It was extracted with ether (3×10 ml) and the combined extracts dried ($MgSO_4$) then evaporated to dryness. The product was purified by flash chromatography using hexanes/ethylacetate. Yield=0.64 g.

Example 43. Conversion of (1'R,2'R)-5'-(methyl-d3)-4-pentyl-2'-(prop-1-en-2-yl-d5)-1',2',3',4'-tetrahydro-[1,1'-biphenyl]-2,6-diol to (6aR,10aR)-6,6,9-tris(methyl-d3)-3-pentyl-6a,7,8,10a-tetrahydro-6H-benzo[c]chromen-1-ol

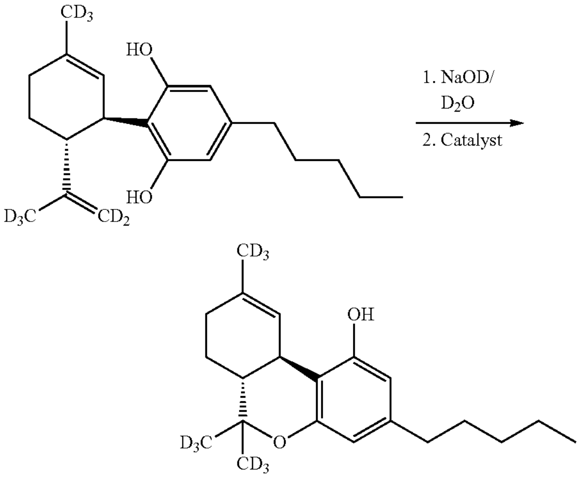

A solution of NaOD in D2O (5 ml of a 0.1 M solution) was added to a solution of (1'R,2'R)-5'-(methyl-d3)-4-pentyl-2'-(prop-1-en-2-yl-d5)-1',2',3',4'-tetrahydro-[1,1'-biphenyl]-2,6-diol (0.51 g, 1.59 mmol) in THF (5 ml) and the mixture was vigorously stirred for 1 hour at room temperature. Ether (10 ml) was added and the phases separated. The organic layer was evaporated to dryness and the residue dissolved in THF (5 ml) and a fresh batch of NaOD in D2O (5 ml of a 0.1 M solution) added. The above procedure was done 5 times to ensure complete deuterium exchange of the OH groups of the substrate. A solution of triisobutylaluminum (0.15 ml of a 1.0 M solution in hexanes, 0.15 mmol) was then added to a solution of the dried residue in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.41 g.

Example 44. Conversion of (1'R,2'R)-5'-(methyl-d3)-2'-(prop-1-en-2-yl-d5)-4-propyl-1',2',3',4'-tetrahydro-[1,1'-biphenyl]-2,6-diol to (6aR,10aR)-6,6,9-tris(methyl-d3)-3-propyl-6a,7,8,10a-tetrahydro-6H-benzo[c]chromen-1-ol

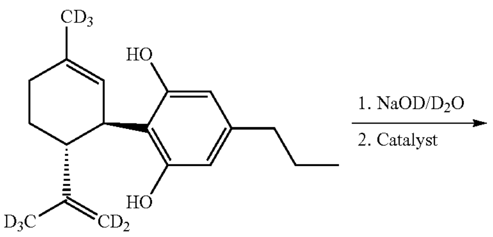

-continued

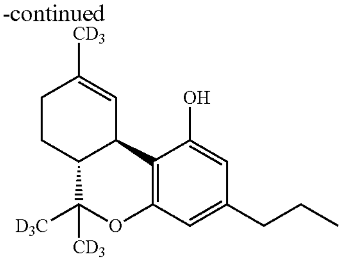

A solution of NaOD in D2O (5 ml of a 0.1 M solution) was added to a solution of (1'R,2'R)-5'-(methyl-d3)-2'-(prop-1-en-2-yl-d5)-4-propyl-1',2',3',4'-tetrahydro-[1,1'-biphenyl]-2,6-diol (0.47 g, 1.59 mmol) in THF (5 ml) and the mixture was vigorously stirred for 1 hour at room temperature. Ether (10 ml) was added and the phases separated. The organic layer was evaporated to dryness and the residue dissolved in THF (5 ml) and a fresh batch of NaOD in D2O (5 ml of a 0.1 M solution) added. The above procedure was done 5 times to ensure complete deuterium exchange of the OH groups of the substrate. A solution of triisobutylaluminum (0.15 ml of a 1.0 M solution in hexanes, 0.15 mmol) was then added to a solution of the dried residue in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.42 g.

Example 45. Conversion of (1'R,2'R)-5'-(methyl-d3)-4-phenethyl-2'-(prop-1-en-2-yl-d5)-1',2',3',4'-tetrahydro-[1,1'-biphenyl]-2,6-diol to (6aR,10aR)-6,6,9-tris(methyl-d3)-3-phenethyl-6a,7,8,10a-tetrahydro-6H-benzo[c]chromen-1-ol

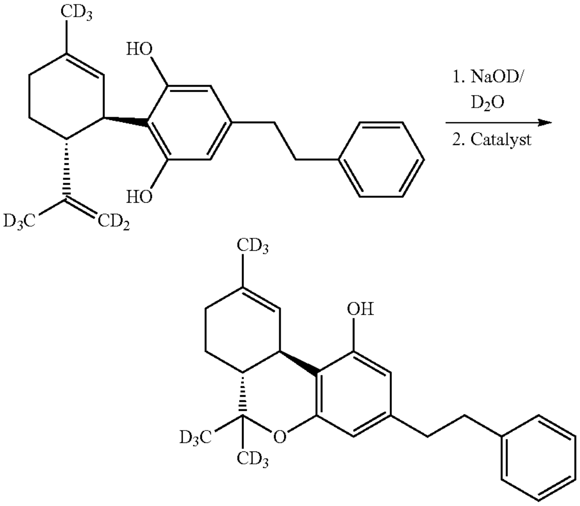

A solution of NaOD in D2O (5 ml of a 0.1 M solution) was added to a solution of (1'R,2'R)-5'-(methyl-d3)-4-phenethyl-2'-(prop-1-en-2-yl-d5)-1',2',3',4'-tetrahydro-[1,1'-biphenyl]-2,6-diol (0.57 g, 1.59 mmol) in THF (5 ml) and the mixture was vigorously stirred for 1 hour at room temperature. Ether (10 ml) was added and the phases separated. The organic layer was evaporated to dryness and the residue dissolved in THF (5 ml) and a fresh batch of NaOD in D2O (5 ml of a 0.1 M solution) added. The above procedure was done 5 times to ensure complete deuterium exchange of the OH groups of the substrate. A solution of triisobutylaluminum (0.15 ml of a 1.0 M solution in hexanes, 0.15 mmol) was then added to a solution of the dried residue in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.51 g.

Example 46. Conversion of (1'R,2'R)-5'-methyl-4-pentyl-2'-(prop-1-en-2-yl-d5)-1',2',3',4'-tetrahydro-[1,1'-biphenyl]-2,6-diol to (6aR,10aR)-9-methyl-6,6-bis(methyl-d3)-3-pentyl-6a,7,8,10a-tetrahydro-6H-benzo[c]chromen-1-ol

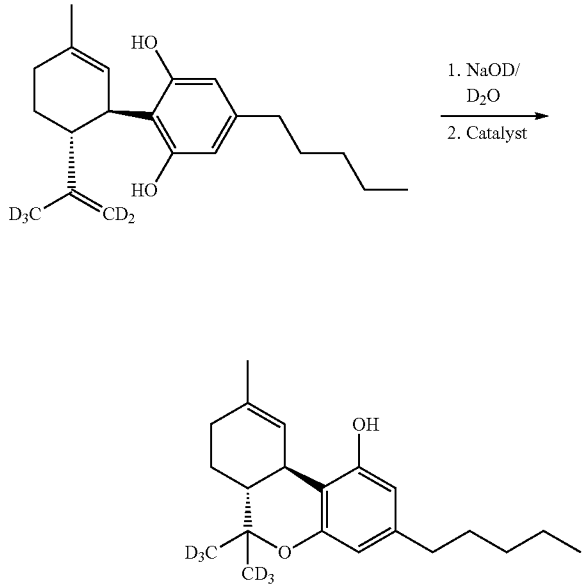

A solution of NaOD in D2O (5 ml of a 0.1 M solution) was added to a solution of (1'R,2'R)-5'-methyl-4-pentyl-2'-(prop-1-en-2-yl-d5)-1',2',3',4'-tetrahydro-[1,1'-biphenyl]-2,6-diol (0.51 g, 1.59 mmol) in THF (5 ml) and the mixture was vigorously stirred for 1 hour at room temperature. Ether (10 ml) was added and the phases separated. The organic layer was evaporated to dryness and the residue dissolved in THF (5 ml) and a fresh batch of NaOD in D2O (5 ml of a 0.1 M solution) added. The above procedure was done 5 times to ensure complete deuterium exchange of the OH groups of the substrate. A solution of triisobutylaluminum (0.15 ml of a 1.0 M solution in hexanes, 0.15 mmol) was then added to a solution of the dried residue in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.42 g.

Example 47. Conversion of (1'R,2'R)-5'-methyl-2'-(prop-1-en-2-yl-d5)-4-propyl-1',2',3',4'-tetrahydro-[1,1'-biphenyl]-2,6-diol to (6aR,10aR)-9-methyl-6,6-bis(methyl-d3)-3-propyl-6a,7,8,10a-tetrahydro-6H-benzo[c]chromen-1-ol

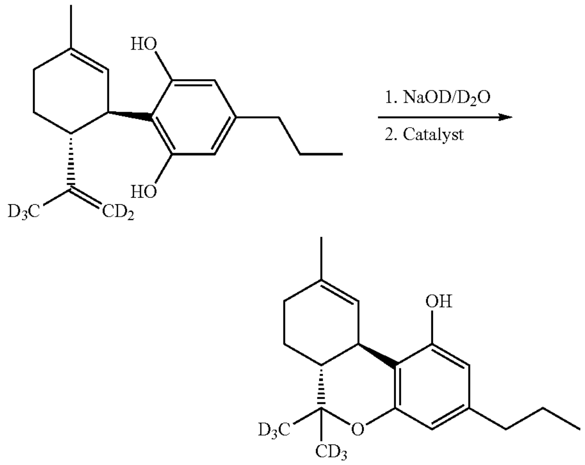

A solution of NaOD in D2O (5 ml of a 0.1 M solution) was added to a solution of (1'R,2'R)-5'-methyl-2'-(prop-1-en-2-yl-d5)-4-propyl-1',2',3',4'-tetrahydro-[1,1'-biphenyl]-2,6-diol (0.46 g, 1.59 mmol) in THF (5 ml) and the mixture was vigorously stirred for 1 hour at room temperature. Ether (10 ml) was added and the phases separated. The organic layer was evaporated to dryness and the residue dissolved in THF (5 ml) and a fresh batch of NaOD in D2O (5 ml of a 0.1 M solution) added. The above procedure was done 5 times to ensure complete deuterium exchange of the OH groups of the substrate. A solution of triisobutylaluminum (0.15 ml of a 1.0 M solution in hexanes, 0.15 mmol) was then added to a solution of the dried residue in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.39 g.

Example 48. Conversion of (1'R,2'R)-5'-methyl-4-phenethyl-2'-(prop-1-en-2-yl-d5)-1',2',3',4'-tetrahydro-[1,1'-biphenyl]-2,6-diol to (6aR,10aR)-9-methyl-6,6-bis(methyl-d3)-3-phenethyl-6a,7,8,10a-tetrahydro-6H-benzo[c]chromen-1-ol

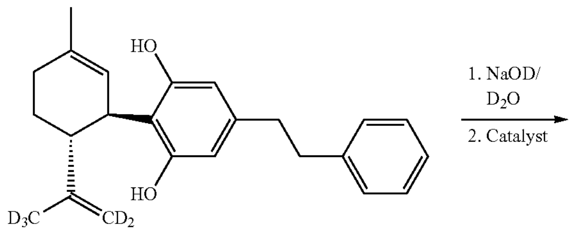

-continued

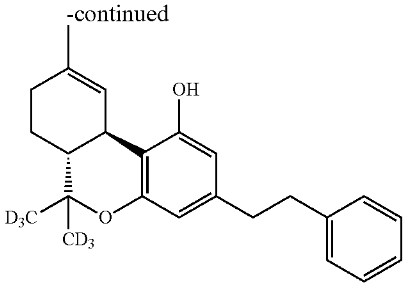

A solution of NaOD in D2O (5 ml of a 0.1 M solution) was added to a solution of (1'R,2'R)-5'-methyl-4-phenethyl-2'-(prop-1-en-2-yl-d5)-1',2',3',4'-tetrahydro-[1,1'-biphenyl]-2,6-diol (0.56 g, 1.59 mmol) in THF (5 ml) and the mixture was vigorously stirred for 1 hour at room temperature. Ether (10 ml) was added and the phases separated. The organic layer was evaporated to dryness and the residue dissolved in THF (5 ml) and a fresh batch of NaOD in D2O (5 ml of a 0.1 M solution) added. The above procedure was done 5 times to ensure complete deuterium exchange of the OH groups of the substrate. A solution of triisobutylaluminum (0.15 ml of a 1.0 M solution in hexanes, 0.15 mmol) was then added to a solution of the dried residue in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.50 g.

Example 49. Conversion of (1'R,2'R)-5'-(methyl-d3)-4-pentyl-2'-(prop-1-en-2-yl)-1',2',3',4'-tetrahydro-[1,1'-biphenyl]-2,6-diol to (6aR,10aR)-6,6-dimethyl-9-(methyl-d3)-3-pentyl-6a,7,8,10a-tetrahydro-6H-benzo[c]chromen-1-ol

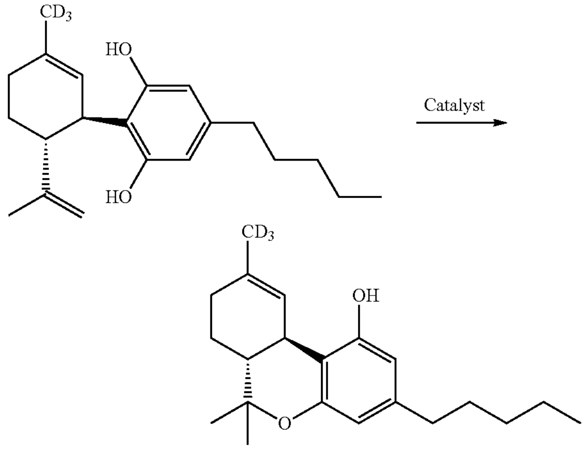

A solution of triisobutylaluminum (0.15 ml of a 1.0 M solution in hexanes, 0.15 mmol) was added to a solution of (1'R,2'R)-5'-(methyl-d3)-4-pentyl-2'-(prop-1-en-2-yl)-1',2',3',4'-tetrahydro-[1,1'-biphenyl]-2,6-diol (0.50 g, 1.59 mmol) in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.38 g.

Example 50. Conversion of (1'R,2'R)-5'-(methyl-d3)-2'-(prop-1-en-2-yl)-4-propyl-1',2',3',4'-tetrahydro-[1,1'-biphenyl]-2,6-diol to (6aR,10aR)-6,6-dimethyl-9-(methyl-d3)-3-propyl-6a,7,8,10a-tetrahydro-6H-benzo[c]chromen-1-ol

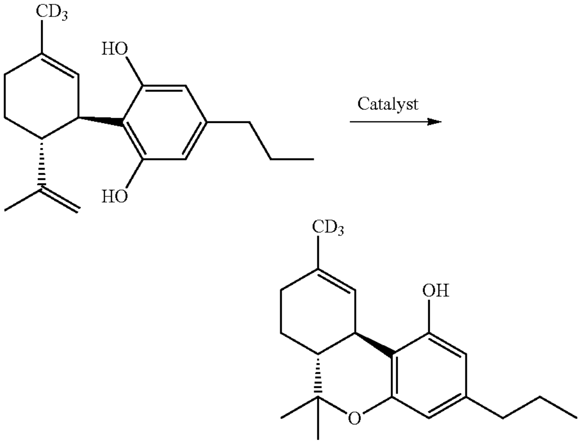

A solution of triisobutylaluminum (0.15 ml of a 1.0 M solution in hexanes, 0.15 mmol) was added to a solution of (1'R,2'R)-5'-(methyl-d3)-2'-(prop-1-en-2-yl)-4-propyl-1',2',3',4'-tetrahydro-[1,1'-biphenyl]-2,6-diol (0.46 g, 1.59 mmol) in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.37 g.

Example 51. Conversion of (1'R,2'R)-5'-(methyl-d3)-4-phenethyl-2'-(prop-1-en-2-yl)-1',2',3',4'-tetrahydro-[1,1'-biphenyl]-2,6-diol to (6aR,10aR)-6,6-dimethyl-9-(methyl-d3)-3-phenethyl-6a,7,8,10a-tetrahydro-6H-benzo[c]chromen-1-ol

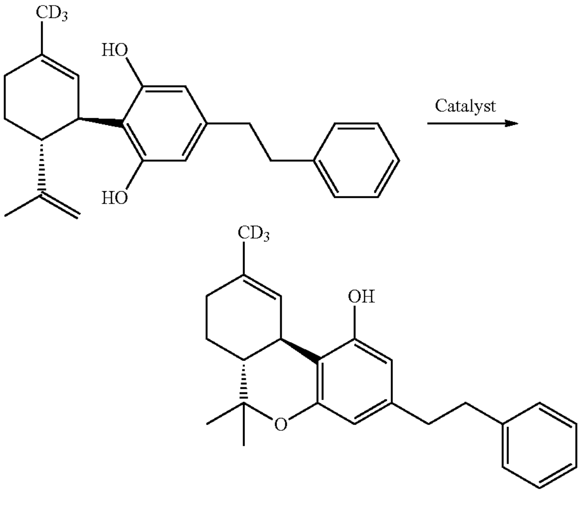

A solution of triisobutylaluminum (0.15 ml of a 1.0 M solution in hexanes, 0.15 mmol) was added to a solution of (1'R,2'R)-5'-(methyl-d3)-4-phenethyl-2'-(prop-1-en-2-yl)-1', 2',3',4'-tetrahydro-[1,1'-biphenyl]-2,6-diol (0.56 g, 1.59 mmol) in dry dichloromethane (5 ml) and the mixture stirred at room temperature for 15 hours. The reaction was quenched with ammonium chloride solution and diethyl ether added. The phases were separated, and the organic layer was dried ($MgSO_4$), filtered and evaporated to dryness. Yield=0.48 g.

While the foregoing disclosure has been described in some detail for purposes of clarity and understanding, it will be appreciated by one skilled in the art, from a reading of the disclosure that various changes in form and detail can be made without departing from the true scope of the disclosure in the appended claims.

All publications, patents, and patent applications are herein incorporated by reference in their entirety to the same extent as if each individual publication, patent or patent application was specifically and individually indicated to be incorporated by reference in its entirety.

What is claimed is:

1. A compound of the Formula (I):

(I)

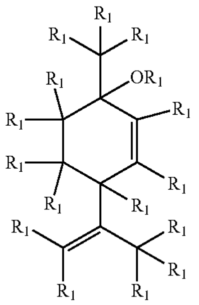

wherein, the $R_1$ groups are independently or simultaneously selected from the group consisting of hydrogen and deuterium; and at least one $R_1$ is deuterium-enriched and optionally carbon-13- or carbon-14-enriched.

2. The compound of Formula (I) according to claim 1:

(I)

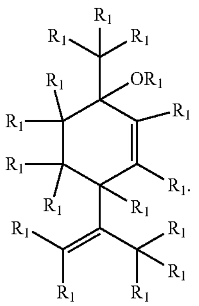

wherein at least one of the carbon atoms connected to at least one $R_1$ of Formula (I) is carbon-13 or carbon-14 enriched.

3. The compound of Formula (I) according to claim 1, wherein the compound of Formula (I) is a compound of Formula (II) to Formula (X):

(II)

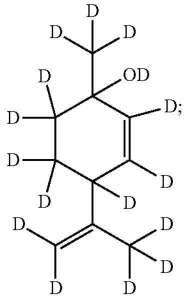

(III)

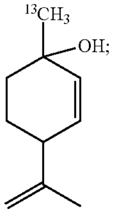

(IV)

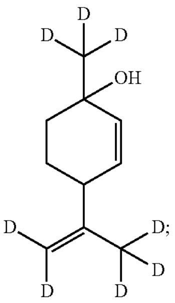

(V)

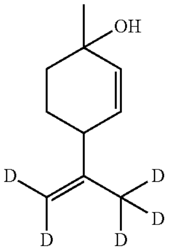

(VI)

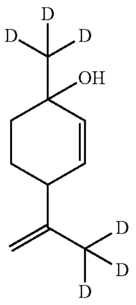

-continued (VII)

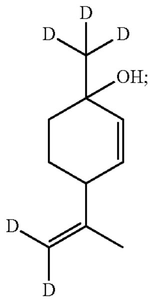

(VIII)

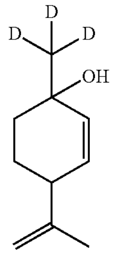

(IX)

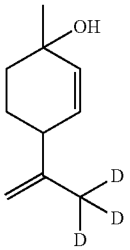

(X)

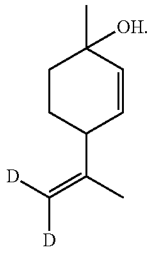

4. The compound of Formula (I) according to claim 1, wherein the compounds are single enantiomers, mixture of enantiomers, individual diastereomers, or mixture of diastereomers.

5. A process for the preparation of a compound of Formula (I) of claim 1, comprising:

(a) reacting a limonene precursor with a N-halosuccinimide to prepare a halohydrin; wherein halo represents fluoro, chloro, bromo, or iodo;

(b) reacting the halohydrin with a base to prepare trans-limonene oxide or a derivative;

(c) reacting the trans-limonene oxide or derivative with $(R_9)_2NH$ to prepare an aminoalcohol;

wherein $R_9$ represents hydrogen, optionally substituted $C_1$-$C_{20}$-alkyl, optionally substituted $C_2$-$C_{20}$-alkenyl, optionally substituted $C_2$-$C_{20}$-alkynyl, optionally substituted $C_3$-$C_{20}$-cycloalkyl, or optionally substituted $C_6$-$C_{14}$-aryl;

(d) converting the aminoalcohol to a compound of Formula (I), by reacting the aminoalcohol with hydrogen peroxide and heat.

6. The process of claim 5, for the preparation of a compound of Formula (I), wherein the limonene is a deuterated-, carbon-13- and/or carbon-14 enriched analogue of limonene.

7. A compound according to claim 1 or 2, in which the deuterium enrichment in compounds of Formula (I) is between 1% and 100% at the specified position, and the carbon-13 enrichment is between 5% and 100% at the specified position.

8. A compound according to claim 2, in which the carbon-14 enrichment in compounds of Formula (I) is between 1 part per billion to 100% at the specified position.

9. A compound according to claim 1 or 2, in which the deuterium, carbon-13 or carbon-14 enrichment is no less than 100% at the specified position.

10. The compound of Formula (I) according to claim 1, wherein the compound is

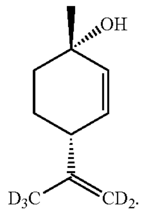

* * * * *